(12) United States Patent
Huang et al.

(10) Patent No.: US 8,906,322 B2
(45) Date of Patent: **\*Dec. 9, 2014**

(54) METHOD FOR CONTINUOUS PARTICLE SEPARATION USING OBSTACLE ARRAYS ASYMMETRICALLY ALIGNED TO FIELDS

(71) Applicant: The Trustees of Princeton University, Princeton, NJ (US)

(72) Inventors: Lotien Richard Huang, Brookline, NJ (US); James Christopher Sturm, Princeton, NJ (US); Robert Hamilton Austin, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,239

(22) Filed: Oct. 8, 2012

(65) Prior Publication Data
US 2013/0168298 A1 Jul. 4, 2013

Related U.S. Application Data

(63) Continuation of application No. 13/180,823, filed on Jul. 12, 2011, now Pat. No. 8,282,799, which is a continuation of application No. 11/640,111, filed on Dec. 15, 2006, now Pat. No. 7,988,840, which is a continuation of application No. 10/693,091, filed on Oct. 23, 2003, now Pat. No. 7,150,812.

(60) Provisional application No. 60/420,756, filed on Oct. 23, 2002.

(51) Int. Cl.
| | | |
|---|---|---|
| B01L 3/00 | (2006.01) | |
| G01N 27/447 | (2006.01) | |
| G01N 27/44 | (2006.01) | |
| B07B 1/00 | (2006.01) | |
| G01N 30/02 | (2006.01) | |
| G01N 30/00 | (2006.01) | |
| G01N 30/60 | (2006.01) | |

(52) U.S. Cl.
CPC . *B07B 1/00* (2013.01); *G01N 30/02* (2013.01); *G01N 27/44773* (2013.01); *B01L 3/5027* (2013.01); *G01N 27/44791* (2013.01); *G01N 27/44704* (2013.01); *G01N 30/0005* (2013.01); *G01N 30/6095* (2013.01)
USPC ............................ 422/503; 204/451; 204/601

(58) Field of Classification Search
USPC ............ 209/635, 155; 204/451, 601; 422/503
See application file for complete search history.

(56) References Cited

U.S. PATENT DOCUMENTS

| | | | |
|---|---|---|---|
| 5,427,663 A | 6/1995 | Austin et al. | |
| 5,715,946 A * | 2/1998 | Reichenbach | 209/156 |

(Continued)

OTHER PUBLICATIONS

Defintion of "array" downloaded from www.mathisfun.com/definitions/array.html on Apr. 7, 2014.*

(Continued)

*Primary Examiner* — Alex Noguerola
(74) *Attorney, Agent, or Firm* — Kilpatrick Townsend & Stockton LLP

(57) ABSTRACT

The present invention relates to methods and devices for separating particles according to size. More specifically, the present invention relates to a microfluidic method and device for the separation of particles according to size using an array comprising a network of gaps, wherein the field flux from each gap divides unequally into subsequent gaps. In one embodiment, the array comprises an ordered array of obstacles in a microfluidic channel, in which the obstacle array is asymmetric with respect to the direction of an applied field.

20 Claims, 31 Drawing Sheets

(56) References Cited

U.S. PATENT DOCUMENTS

| | | | |
|---|---|---|---|
| 5,837,115 A | | 11/1998 | Austin et al. |
| 5,885,470 A | * | 3/1999 | Parce et al. ............... 216/33 |
| 6,632,652 B1 | | 10/2003 | Austin et al. |
| 6,762,059 B2 | | 7/2004 | Chan et al. |
| 7,150,812 B2 | | 12/2006 | Huang et al. |
| 7,735,652 B2 | | 6/2010 | Inglis et al. |
| 7,988,840 B2 | | 8/2011 | Huang et al. |
| 8,282,799 B2 | | 10/2012 | Huang et al. |

OTHER PUBLICATIONS

Oart of the defintion of "array" downloaded from www.wiki.scratch.mit.edu on Apr. 7, 2014.*

Chou, C., et al., "Sorting by Diffusion: An Asymmetric Obstacle Course for Continuous Molecular Separation," Proceedings of the National Academy of Sciences., vol. 96, Nov. 23, 1999, 4 pages.

Duke, T., et al. "Microfabricated Sieve for the Continuous Sorting of Macromolecurles," Physical Review Letters, vol. 80, Feb. 16, 1998. 4 pages.

Ertas, D. "Lateral Separation of Macromolecules and Polyeletrolytes in Microlithographic Arrays," Harvard University, Feb. 1, 2008, 4 pages.

Han, J., et al. "Separation of Long DNA Molecules in a Microfabricated Entropic Trap Array," Science, vol. 288, May 12, 2000, 4 pages.

Huang, L., et al. "Role of Molecular Size in Ratchet Fractionation," Physical Review Letters, vol. 89, Oct. 21, 2002, 4 pages.

Turner, S., et al. "Confinement-Induced Entropic Reciol of Single DNA Molecules in a Nanofluidic Structure," Physical Review Letters, vol. 88, Mar. 25, 2002, 4 pages.

Ashcroft, N., et al., "Solid State Physics," Saunders College Publishing, Fort Worth, only Table of Contents and List of Important Tables, 1976.

Becker, W., et al., "Fabrication of microstructures with height aspect ratios and great structural heights by synchrotron radiation lithography, galvanoforming, and plastic moulding (L1GA process)," Microelectronic Engineering, 4(1), May 1986, pp. 35-36.

Becker, H., et al., "Planar Quartz Chips with Submicron Channels for Two-Dimensional Capillary Electrophoresis Applications," J. Micromech. Microeng., 8(1), Mar. 1998, pp. 24-28.

Berg, H., "Random Walks in Biology," Princeton University Press, New Jersey, 1993, p. 56, Table of Contents and pp. 51-58.

Giddings, J., "Unified Separation Science," Wiley, New York, 1991, Table of Contents and pp. xi-xv.

Giddings, J., "Eddy's diffusion in chromatography," Nature, Aug. 1, 1959, pp. 357-358.

Giddings, J., "Field-flow fractionation: Analysis of macromolecular, colloidal, and particulate materials," Science, Jun. 4, 1993, pp. 1456-1465.

Huang, L., et al., "A DNA prism for high-speed continuous fractionation of large DNA molecules," Nat. Biotechnol, 20(10), Oct. 2002, pp. 1048-1051.

* cited by examiner

METHOD FOR CONTINUOUS PARTICLE SEPARATION USING OBSTACLE ARRAYS ASYMMETRICALLY ALIGNED TO FIELDS

CROSS-REFERENCE TO RELATED APPLICATIONS

This application is a continuation of U.S. Pat. No. 8,282,799 filed Jul. 12, 2011, issued Oct. 9, 2012, entitled "METHOD FOR CONTINUOUS PARTICLE SEPARATION USING OBSTACLE ARRAYS ASYMMETRICALLY ALIGNED TO FIELDS," which is a continuation of U.S. Pat. No. 7,988,840 filed Dec. 15, 2006, issued Aug. 2, 2011, entitled "METHOD FOR CONTINUOUS PARTICLE SEPARATION USING OBSTACLE ARRAYS ASYMMETRICALLY ALIGNED TO FIELDS," which is a continuation of U.S. Pat. No. 7,150,812 filed Oct. 23, 2003, issued Dec. 19, 2006, entitled "METHOD FOR CONTINUOUS PARTICLE SEPARATION USING OBSTACLE ARRAYS ASYMMETRICALLY ALIGNED TO FIELDS," which claims priority to U.S. Provisional Patent Application No. 60/420,756 filed Oct. 23, 2002, the entire disclosures of which are hereby incorporated by reference, for all purposes, as if fully set forth herein.

STATEMENT REGARDING FEDERALLY SPONSORED RESEARCH OR DEVELOPMENT

This invention was made with government support under Grant #MDA972-00-1-0031 awarded by the Defense Advanced Research Projects Agency (DARPA). The government has certain rights in this invention.

FIELD OF THE INVENTION

The present invention relates to methods and devices for separating particles according to size. More specifically, the present invention relates to a microfluidic method and device for the separation of particles according to size.

BACKGROUND OF THE INVENTION

Separation by size or mass is a fundamental analytical and preparative technique in biology, medicine, chemistry, and industry. Conventional methods include gel electrophoresis, field-flow fractionation, sedimentation and size exclusion chromatography [J. C. Giddings, Unified Separation Science (Wiley, New York, 1991)]. Gel electrophoresis utilizes an electric field to drive charged molecules to be separated through a gel medium, which serves as a sieving matrix. The molecules are initially loaded at one end of a gel matrix, and are separated into component zones as they migrate through the gel. Field-flow fractionation is carried out in a thin ribbon-like channel, in which the flow profile is parabolic. Particles are loaded as a sample zone, and then flow through the channel. Separation occurs as particles of different properties flow in different positions of the flow, due to the influence of a field, resulting in different migration speeds. The field is applied perpendicular to the flow. Sedimentation utilizes gravitational or centrifugal acceleration to force particles through a fluid. Particles migrate through the fluid at different speeds, depending on their sizes and densities, and thus are separated. Size exclusion chromatography (SEC) utilizes a tube packed with porous beads, through which sample molecules are washed. Molecules smaller than the pores can enter the beads, which lengthen their migration path, whereas those larger than the pores can only flow between the beads. In this way smaller molecules are on average retained longer and thus become separated from larger molecules. Zones broaden, however, as they pass through the column, because there are many possible migration paths for each molecule and each path has a different length, and consequently a different retention time. This multipath zone broadening (Eddy diffusion) is a major factor limiting resolution. J. C. Giddings, Unified Separation Science (John Wiley & Sons, New York, 1991). Other methods for separation according to size, including gel electrophoresis, field-flow fractionation, also involve stochastic processes, which may limit their resolution. J. C. Giddings, Nature 184, 357 (1959); J. C. Giddings, Science 260, 1456 (1993).

The need for reliable and fast separation of large biomolecules such as DNA and proteins cannot be overemphasized. Recently, micro/nano-fabricated structures exploiting various ideas for DNA separation have been demonstrated. The use of micro/nano-fabricated structures as sieving matrices for particle separation was disclosed in U.S. Pat. No. 5,427,663. According to this document, DNA molecules are separated as they are driven by electric fields through an array of posts. U.S. Pat. No. 5,427,663 discloses a sorting apparatus and method for fractionating and simultaneously viewing individual microstructures and macromolecules, including nucleic acids and proteins. According to U.S. Pat. No. 5,427,663, a substrate having a shallow receptacle located on a side thereof is provided, and an array of obstacles outstanding from the floor of the receptacles is provided to interact with the microstructures and retard the migration thereof. To create migration of the microstructures, electrodes for generating electric fields in the fluid are made on two sides of the receptacle. This is analogous to the conventional gel electrophoresis. However, micromachined structures are substituted for gel as sieving matrices.

A variety of microfabricated sieving matrices have been disclosed. In one design, arrays of obstacles sort DNA molecules according to their diffusion coefficients using an applied electric field [Chou, C. F. et. al., Proc. Natl. Acad. Sci. 96, 13762 (1999).]. The electric field propels the molecules directly through the gaps between obstacles, wherein each gap is directly below another gap. The obstacles are shaped so that diffusion is biased in one direction as DNA flows through the array. After flowing through many rows of obstacles, DNA with different diffusion coefficients are deflected to different positions. However, because the diffusion coefficient is low for large molecules, the asymmetric obstacle arrays are slow, with running times of typically more than 2 hours. In a second design, entropic traps consisting of a series of many narrow constrictions (<100 nm) separated by wider and deeper regions (a few microns), reduce the separation time to about 30 minutes [Han, J. & Craighead, H. G., Science 288, 1026 (2000).]. Because the constrictions are fabricated to be narrower than the radius of gyration of DNA molecules to be separated, they act as entropic barriers. The probability of a molecule overcoming the entropic barrier is dependent on molecular weight, and thus DNA molecules migrate in the entropic trap array with different mobilities. Larger molecules, with more degrees of configurational freedom, migrate faster in these devices. In a third design, a hexagonal array of posts acts as the sieving matrix in pulsed-field electrophoresis for separation of DNA molecules in the 100 kb range [Huang, L. R., Tegenfeldt, J. O., Kraeft, J. J., Sturm, J. C., Austin, R. H. and Cox, E. C., Nat Biotechnol. 20, 1048 (2002).]. However, these devices generally require features sizes comparable to or smaller than the molecules being fractionated. Han, J. & Craighead, H. G. Separation of long DNA molecules in a microfabricated entropic trap array. Science 288, 1026-1029 (2000); Turner, S. W., Cabodi, M., Craighead, H. G. Confinement-induced entropic recoil of single DNA molecules in a nanofluidic structure. Phys Rev Lett. 2002 Mar. 25; 88(12):128103; Huang, L. R., Tegenfeldt, J. O., Kraeft, J. J., Sturm, J. C., Austin, R. H. and Cox, E. C. A DNA prism for high-speed continuous fractionation of large DNA molecules. Nat Biotechnol. 2002 October; 20(10):1048-51; and Huang, L. R., Silberzan, P., Tegenfeldt, J. O., Cox, E. C., Sturm, J. C., Austin, R. H. and Craighead, H. Role of molecular size in ratchet fractionation. Phys. Rev. Lett. 89, 178301 (2002). The need for small feature size may have the following detrimental effects: (i) the devices cannot fractionate small molecules such as proteins, (ii) the devices may have very low throughput, and thus are not useful sample preparation tools, (iii) the devices can only analyze very small volume of samples, and therefore usually require concentrated samples or expensive equipment for sample detection, and (iv) manufacturing the devices require state-of-the-art fabrication techniques, and thus high cost.

BRIEF DESCRIPTION OF THE INVENTION

The present invention provides a microfluidic device for separating particles according to size comprising a microfluidic channel, and an array comprising a network of gaps within the microfluidic channel. The device employs a field that propels the particles being separated through the microfluidic channel. The individual field flux exiting a gap is divided unequally into a major flux component and a minor flux component into subsequent gaps in the array, such that the average direction of the major flux components is not parallel to the average direction of the field.

In a preferred embodiment, the present invention provides a microfluidic device for separating particles according to size comprising a microfluidic channel, and an ordered array of obstacles within the microfluidic channel. The ordered array of obstacles is asymmetric with respect to the average direction of the applied field. The device employs a field that propels the particles being separated through the microfluidic channel.

The present invention also provides a method for separating particles comprising introducing the particles to be separated into an array comprising a network of gaps within the microfluidic channel and applying a field to the particles to propel the particles through the array. A field flux from the gaps is divided unequally into a major flux component and a minor flux component into subsequent gaps in the array, such that the average direction of the major flux components is not parallel to the average direction of the field.

In a preferred embodiment, the present invention also provides a method for separating particles according to size comprising: introducing the particles to be separated into a microfluidic channel comprising an ordered array of obstacles, and applying a field to the particles, wherein the ordered array of obstacles is asymmetric with respect to the average direction of the applied field.

In another embodiment, the present invention provides a microfluidic device for separating particles according to size comprising a microfluidic channel, and multiple arrays in series within the microfluidic channel, wherein each array has a different critical size. The device employs a field that propels the particles being separated through the microfluidic channel. Each of the arrays comprises a network of gaps wherein a flux of the field from the gaps is divided unequally into a major flux component and a minor flux component into subsequent gaps in the network. The average direction of the major flux components in each array is not parallel to the average direction of the field.

BRIEF DESCRIPTION OF THE DRAWINGS

The present invention is described in conjunction with the appended figures.

DETAILED DESCRIPTION OF THE INVENTION

The present invention provides a method and a device for separating particles according to size using an array comprising a network of gaps, wherein the field flux from a gap divides unequally into subsequent gaps. A field is applied to the array to propel the particles being separated through the array. In a preferred embodiment, the array is an ordered array of obstacles in a channel, wherein the array is asymmetric with respect to the direction of the applied field. In further preferred embodiments, the channel that contains the array is a microfluidic channel. The term "channel" as used herein refers to a structure wherein fluid may flow. A channel may be a capillary, a conduit, a strip of hydrophilic pattern on an otherwise hydrophobic surface wherein aqueous fluids are confined, etc. The term "microfluidic" as used herein, refers to a system or device having one or more fluidic channels, conduits or chambers that are generally fabricated at the millimeter to nanometer scale, e.g., typically having at least one cross-sectional dimension in the range of from about 10 nm to about 1 mm.

The present invention is useful for the separation of biological particles according to size, including bacteria, cells, organelles, viruses, nucleic acids (i.e., DNA, etc.), proteins and protein complexes, as well as other nonbiological particles suspended in fluid, such as industrial polymers, powders, latexes, emulsions, and colloids. In addition to particle separation, the method can be used to analyze the size distribution of samples, or extract particles of certain size range from mixtures of particles. Further, because of the large features size, the device may be a high throughput sample preparation tool. The present invention may provide the advantages of low manufacturing cost, high resolution, and improved sample throughput.

Figure 1:
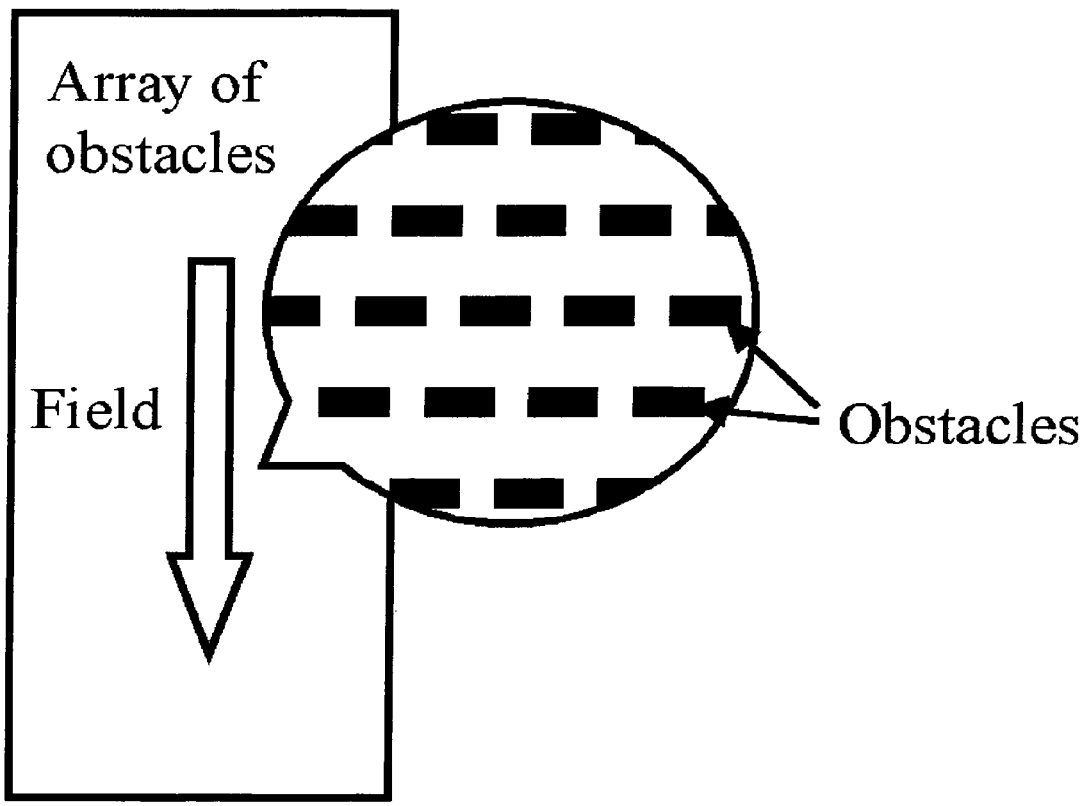
FIG. 1 shows a schematic diagram of an array device according to an embodiment of the present invention. The device consists of an obstacle array asymmetric about the field direction.

In a preferred embodiment, the present invention provides a microfluidic device that separates particles in fluid according to size (for example, see FIG. 1). A field is applied to the particles being separated as the particles pass through the array. The term "field" as used herein refers to any force or vector entity that can be used to propel the particles through the array. The field that drives the particles being separated may be a force field, such as an electric field, a centrifugal field, or a gravitational field. The field that drives the particles being separated may also be a fluid flow, such as a pressure-driven fluid flow, an electro-osmotic flow, capillary action, etc., wherein the vector entity is the fluid flux density. Further, the field may be a combination of a force field and a fluid flow, such as an electro-kinetic flow, which is a combination of the electric field and the electro-osmotic flow. In preferred embodiments, the average direction of the field will be parallel to the walls of the channel that contains the array.

Figure 4:
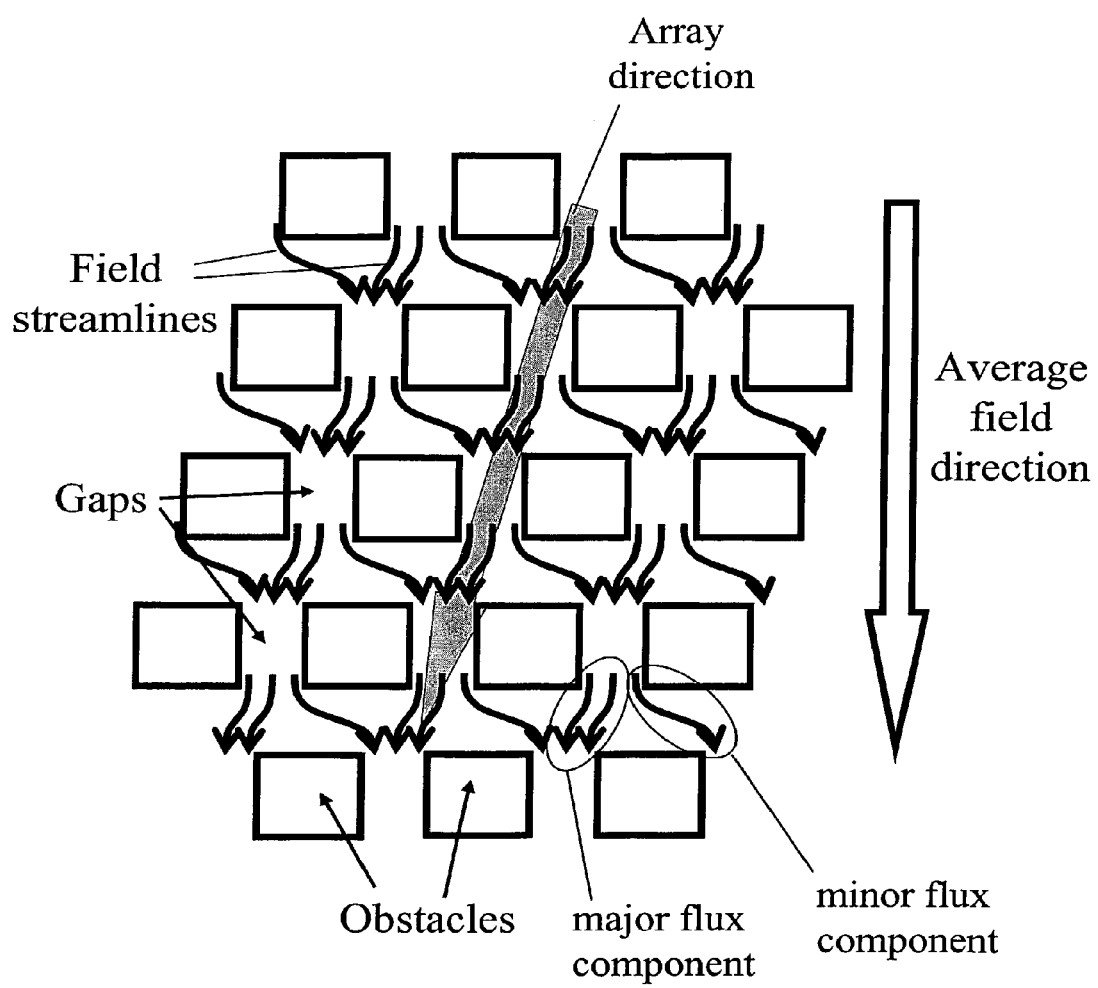
FIG. 4 shows a schematic diagram of an embodiment of the invention, comprising a network of gaps defined by an array of obstacles. Each streamline represents an equal amount of field flux. The field flux from one gap is divided into two subsequent gaps, wherein the amounts of flux going into the two gaps are unequal. In this case, two streamlines goes to the left (major flux component) and one streamline goes to the right (minor flux component) at each gap. The array direction is indicated by the gray arrow.

The array for use in the present invention comprises a network of gaps that creates a field pattern such that the field flux from a gap within the network is divided into unequal amounts (a major flux component and a minor flux component) into the subsequent gaps (for example, see FIG. 4), even though the gaps may be identical in dimensions. Looking at the array as a whole, on average the unequal divisions of the field flux is weighted in one direction. Thus, the major flux components are diverted, on average, in the same direction (i.e., diverted to the same side of the obstacle), such that the average direction of the major flux components is not parallel to the average direction of the minor flux components, or to the average direction of the field. It is preferred that a majority of the major flux components be diverted in the same direction. In a particularly preferred embodiment, the array is an ordered array, wherein the major flux component from each bifurcation event is diverted in the same direction. Generally, the minor flux component exiting one gap feeds into the major flux component exiting a subsequent gap (FIG. 4).

Figure 2:
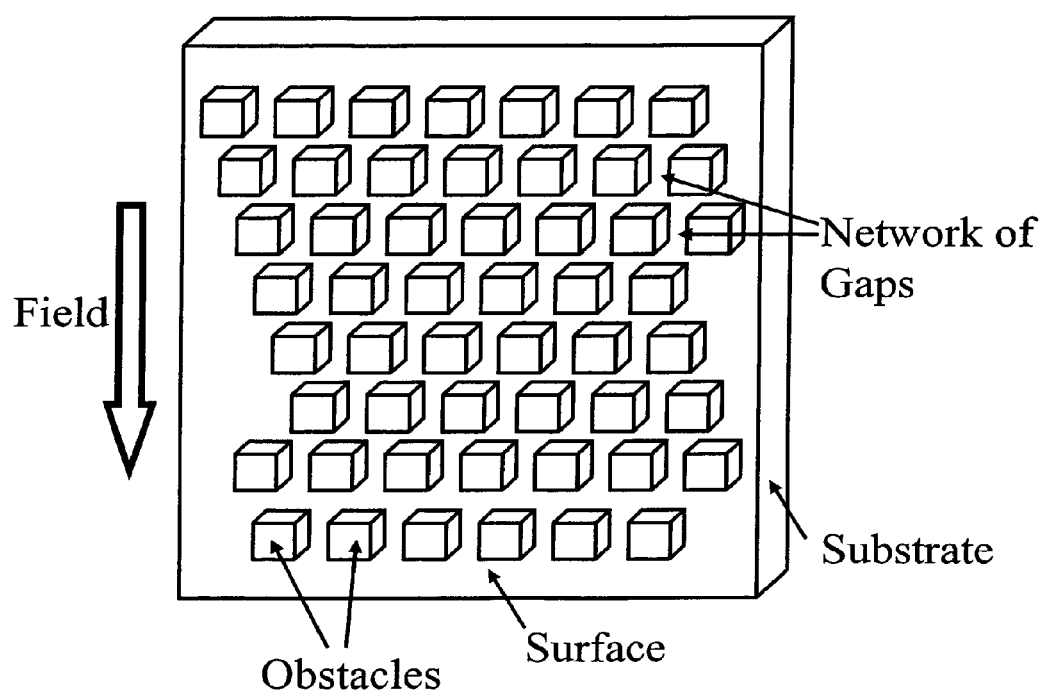
FIG. 2 shows a schematic diagram of a perspective view of a preferred embodiment of the invention, comprising a base substrate with a main surface, on which an obstacle course is made to form a network of gaps, wherein cascades of unequal bifurcations of field flux occur. The obstacle course may be sealed to a cap layer to form an enclosed network of gaps.

The term "gap" as used herein refers to a structure wherein fluids or particles may flow. A gap may be a capillary, a space between two obstacles wherein fluids may flow, a hydrophilic pattern on an otherwise hydrophobic surface wherein aqueous fluids are confined, etc. In a preferred embodiment of the invention, the network of gaps is defined by an array of obstacles. In this embodiment, the gaps would be the space between adjacent obstacles. In a preferred embodiment, the network of gaps will be constructed with an array of obstacles on surface of a substrate (FIG. 2). The term "obstacle" as used herein refers to a physical structure or pattern wherein the particles being separated cannot penetrate, and thus an obstacle may refer to a post outstanding on a base substrate, a hydrophobic barrier for aqueous fluids, etc. In some embodiments, the obstacle may be permeable to the field. For example, an obstacle may be a post made of porous material, wherein the pores allows penetration of the field, but are too small for the particles being separated to enter.

Figure 3:
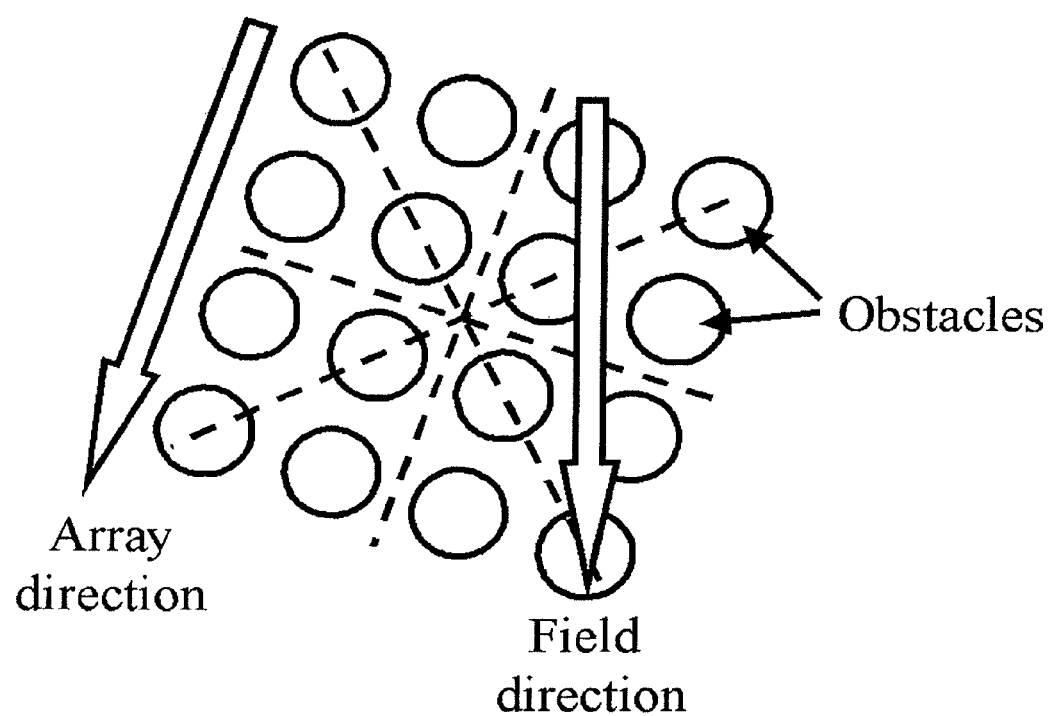
FIG. 3 shows a schematic diagram of an obstacle array. The obstacle array is symmetric about the dotted lines (principle axis), but asymmetric with respect to the field direction.
Figure 6:
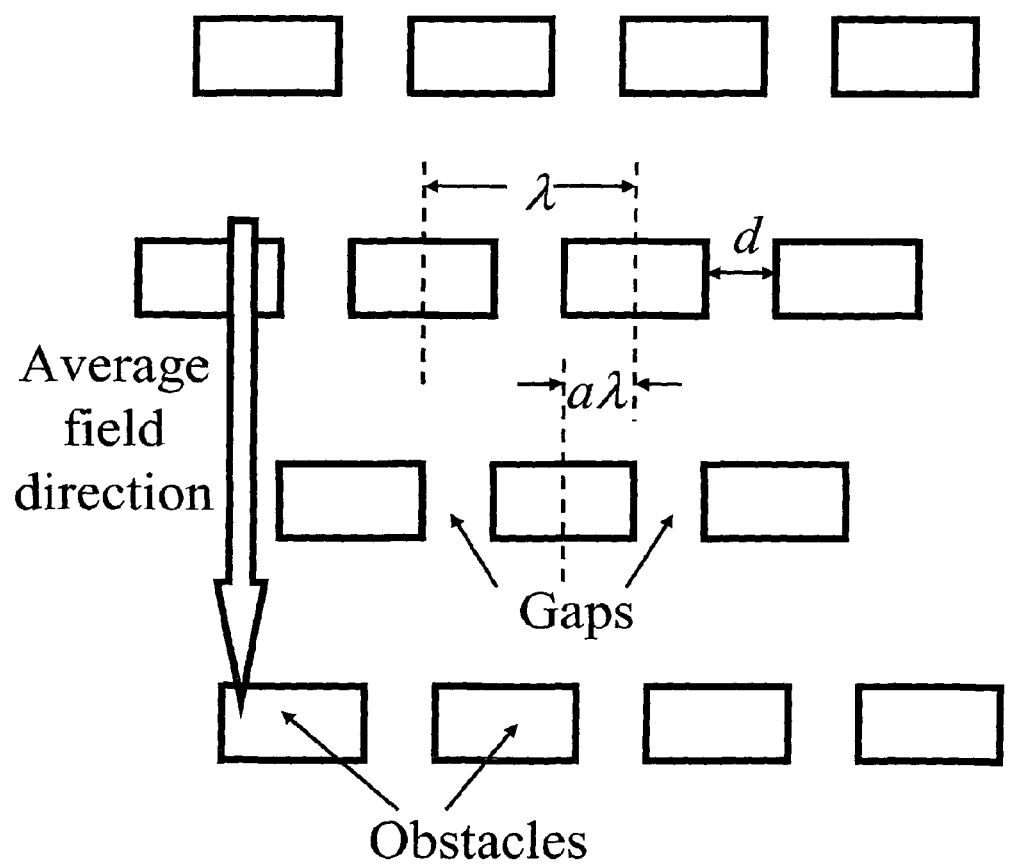
FIG. 6 shows a schematic diagram of an obstacle array, showing characteristic array dimensions. $\lambda$ denotes the period of a row of obstacles, d the gap spacing between obstacles, and $a\lambda$ the lateral shift of every row.

In a preferred embodiment, the network of gaps, wherein the field flux is divided unequally, is formed using a periodic array of obstacles, which is asymmetric with respect to the average direction of the field. An important feature of this embodiment is that the obstacle array is asymmetric with respect to the field, even though the array itself may be symmetric with respect to other axes (FIG. 3). The term asymmetric as used herein refers to an obstacle array in which the field flux from a gap between two obstacles is bifurcated by a subsequent obstacle, such that the bifurcated field flux is not divided into two equal amounts (for example, see the field stream lines of FIG. 4). This may be achieved when the average direction of the field is not parallel to a principle axis of the array (FIG. 3). In one embodiment, an ordered array is tilted at an offset angle θ with respect to the field (for example, FIG. 15), wherein the offset angle θ is selected such that the array is not aligned to the field (i.e., is asymmetric to the field). Alternatively, an asymmetric array may also be achieved using an array comprising rows of obstacles in which each row is laterally shifted from the previous row and the misalignment factor, a, is larger than 0 and smaller than 0.5 (FIG. 6). In a preferred embodiment, the array of obstacles will be an ordered array in which a principle axis of the array is not parallel to the direction of the field (FIG. 3). The term asymmetric refers to the array of obstacles (for example, to the array axis) and not to the shape of individual obstacles. It is preferred that the array is an ordered array in order to maximize the number of bifurcation events that can occur as the sample passes through the array (for example, see FIG. 4).

As used herein, the term "ordered" refers to an array having a generally periodic or repeating spatial arrangement. For example the repeating spatial arrangement, may be square, rectangular, hexagonal, oblique, etc. In other embodiments, the array need not be an ordered array.

Figure 5:
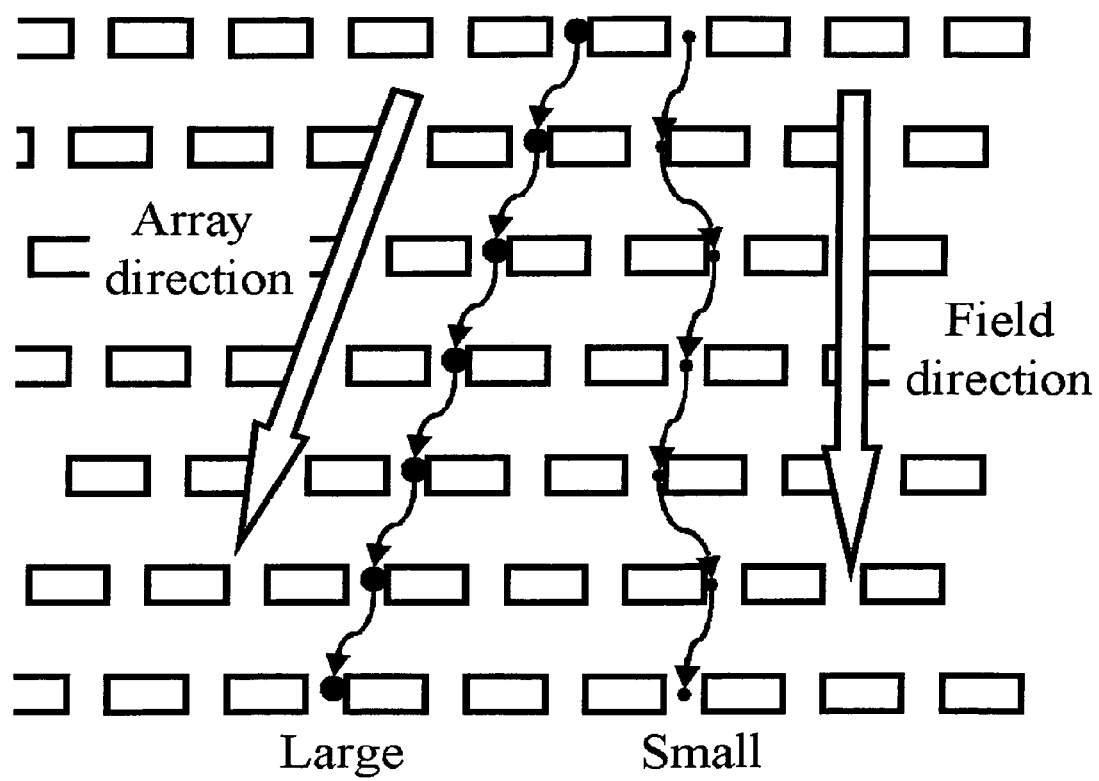
FIG. 5 shows a schematic diagram of particles separated in an array device according to an embodiment of the present invention. The small particles move along field and large ones towards array direction.

In one embodiment of the invention, particles flow through an asymmetric obstacle array, and are separated according to size into different streams (FIG. 5). While small particles follow the field direction, large particles migrate at the array direction. The array direction corresponds to the average direction of the major component of the field flux (for example, see the gray arrow of FIG. 4). The basic theory of the transport process is schematically illustrated in FIG. 5. FIG. 5 depicts one embodiment of an asymmetric array of obstacles in which the array is misaligned (i.e., asymmetric) to the field. For the array type depicted in FIG. 6, the misalignment factor, a, is larger than 0 and smaller than 0.5. When a=0 or a=0.5, the array is symmetric about the field axis. As shown in FIG. 6, each row of obstacles is shifted horizontally with respect to the previous row by a λ, where λ is the center-to-center distance between the obstacles. For the purpose of this discussion, let us assume that a equals ⅓. In preferred embodiments, particles to be separated are driven through the array by a fluid flow. Because of the low Reynolds number in these devices, the flow lines may be laminar, resulting in negligible turbulence and inertial effects.

Figure 7:
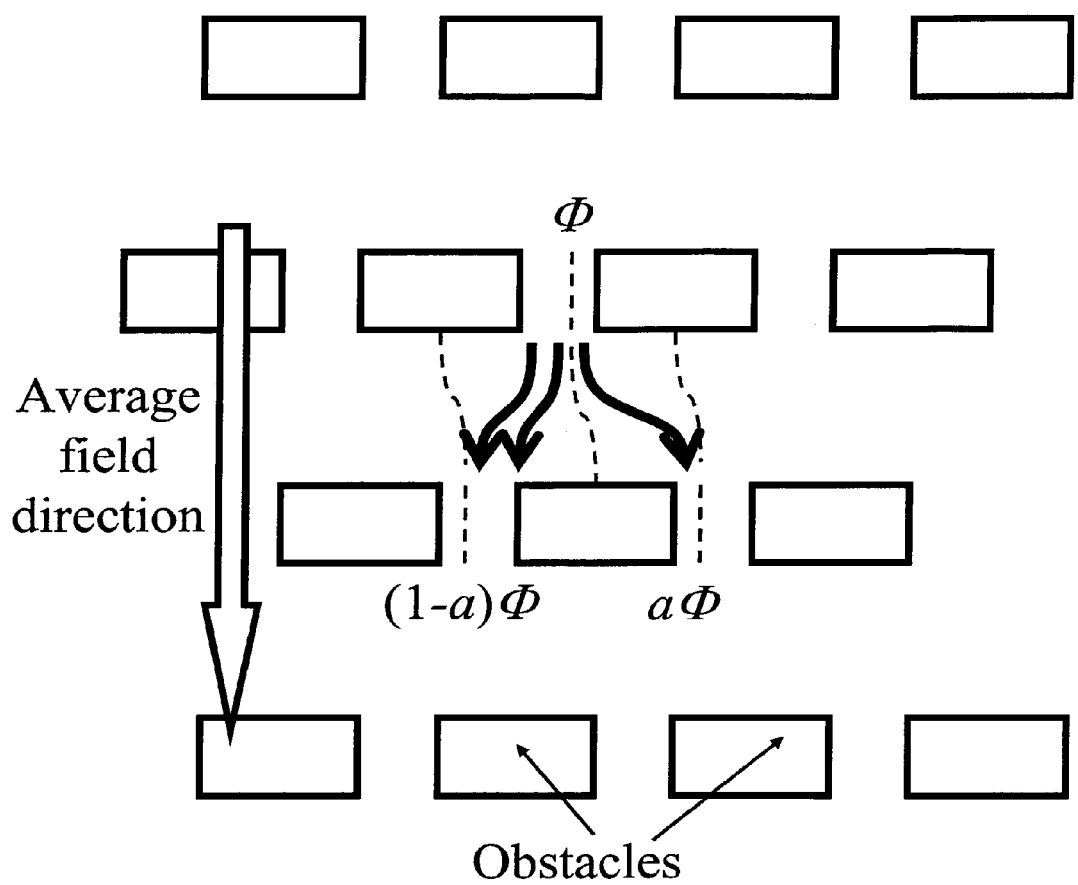
FIG. 7 shows a schematic diagram of a particular array, showing that field lines go around obstacles. The dotted line at the center marks the division of field lines going to different sides of the obstacle.

Because the obstacle array is asymmetrically aligned to the field, i.e., the obstacle lattice is asymmetric with respect to the average field direction, field lines going through one gap have to go around the obstacle in the next row (FIG. 7). To consider the allocation of field lines in the next row, we assume that the field in the gap between obstacles is locally uniform, i.e. field lines are equally spaced in every gap. This may be a good approximation if the field is electrical. This assumption may be relaxed in the case of other fields. The total field flux Φ going through one gap is divided by the subsequent obstacle and splits into two streams, the major flux component and the minor flux component, as the flux goes into the two subsequent gaps (FIG. 7). If that the average field direction is vertical (parallel to the channel walls), Φ. has to go to one gap and $(1-a)\Phi$ to the other. Therefore, unequal division of the field flux occurs at each gap. Generally, the minor flux component exiting one gap feeds into the major flux component exiting a subsequent gap (FIG. 4).

Figure 8:
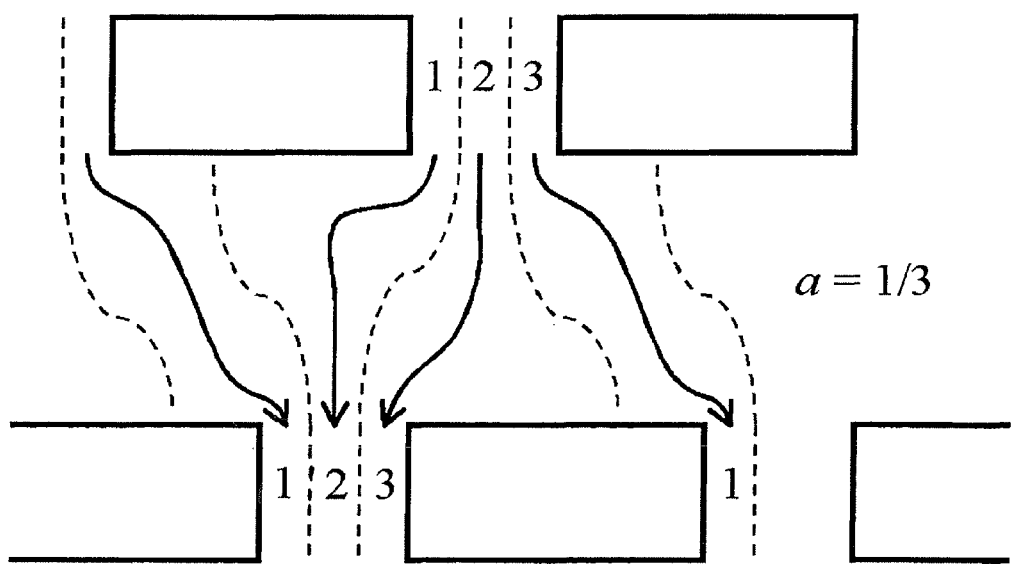
FIG. 8 shows a schematic diagram of a particular array illustrating that field lines shift relative positions in gaps. To illustrate, $a=\frac{1}{3}$ and each gap is divided into three slots, which are denoted 1, 2 and 3. Field lines passing through slot 1 go to slot 2 in the next gap, those through slot 2 go to 3, and the ones through 3 to 1.
Figure 9:
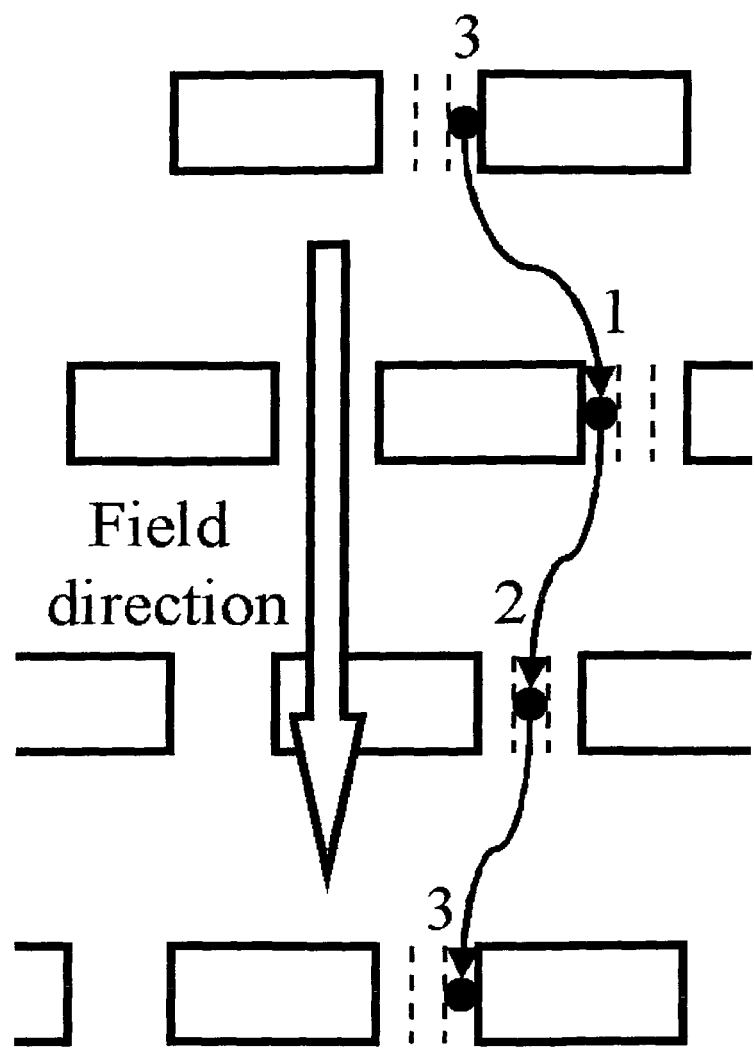
FIG. 9 shows a schematic diagram of a particular array illustrating the path of small particles.

If we divide each gap into 1/a slots (FIG. 8, to illustrate a=⅓), each field line shifts to the next slot as it passes through a row in a cyclic manner: field lines going through position 1 will be at position 2 in the next row, those at position 2 will go to position 3 . . . the ones at position 1/a will go back to position 1. Small particles follow the field and shift from one position to the next in a cyclic manner (FIG. 9). Because small particles may go back to their original slot (relative position in the gap) after 1/a rows, their trajectories follow the field direction and do not disperse after going around many obstacles. Because of the "zigzag" motion of the small particles, this transport pattern may be referred to as the "zigzag mode."

Figure 10:
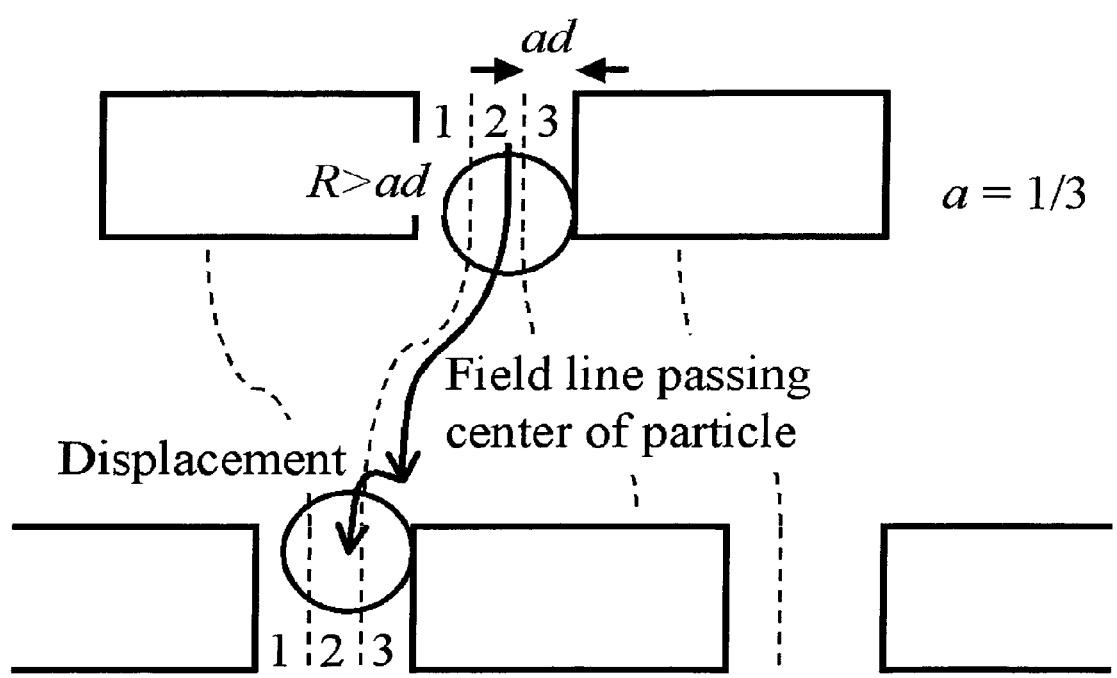
FIG. 10 shows a schematic diagram of a particular array illustrating the displacement of large particles by obstacles.
Figure 11:
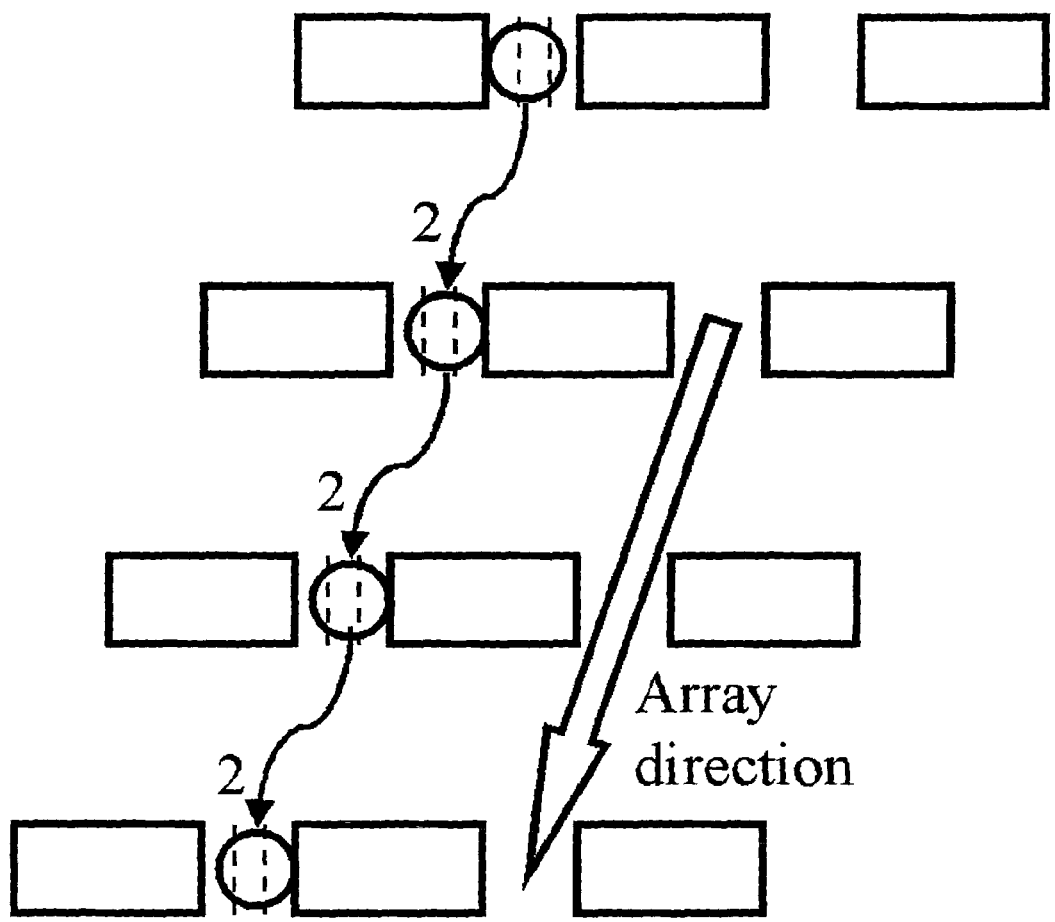
FIG. 11 shows a schematic diagram of a particular array illustrating the path of large particles. Large particles move along the array direction (displacement mode). Note that even if the particle starts at the left side of the gap, eventually it moves to the right side and stays at the right as it is constantly being displaced by obstacles.

In contrast, particles with a large diameter compared to the slot width will not follow individual streamlines, but instead be propelled by many streamlines, which fundamentally changes their final direction of migration. As shown in FIG. 10, a particle in contact with an obstacle and whose characteristic radius R is larger than ad (the width of the gap), will follow a field line going through slot 2, because its center falls in slot 2. Now the field lines goes to slot 3 in the next gap, so the center of the particle should also be in slot 3. However, slot 3 does not have enough room for the particle. Therefore the particle is displaced back to slot 2. This process may be repeated every time as a large particle approaches a row of obstacles. Because large particles are displaced from slot 3 to slot 2, they follow the array direction (FIG. 11). The motion of large particles through the array is termed the "displacement" mode.

Figure 12:
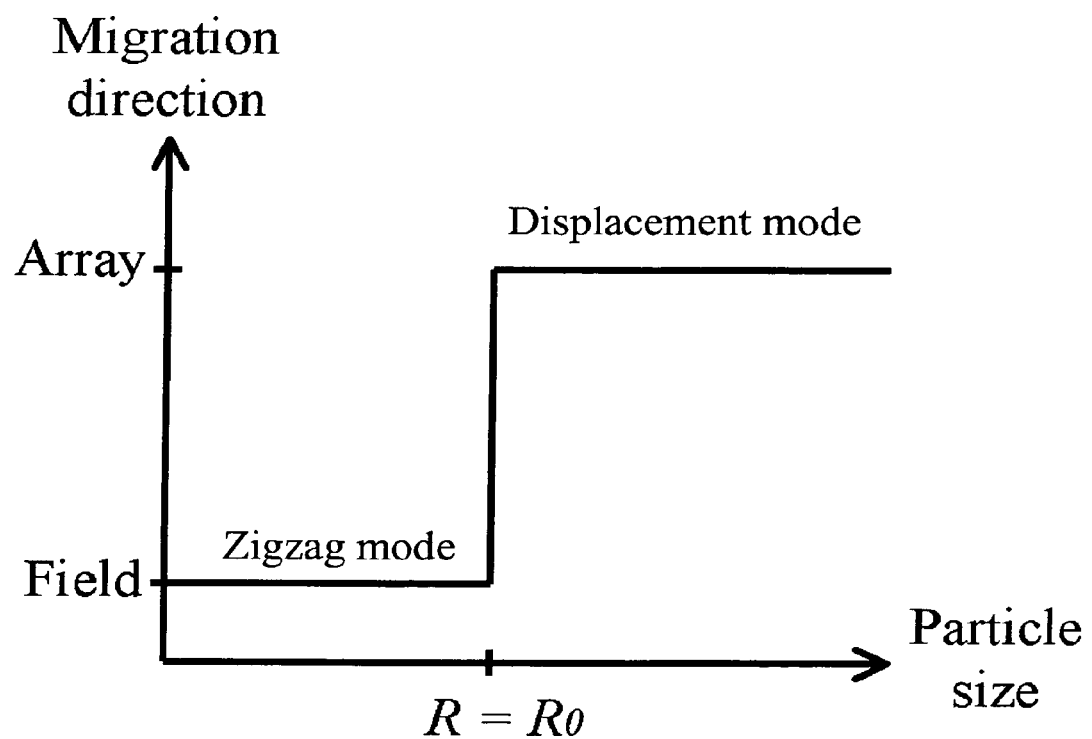
FIG. 12 shows a plot of particle migration direction vs. their size. There exists a critical particle $R_0$ where a sharp transition of migration direction occurs.

In summary, there exists a critical particle radius $R_D$ above which particles move in the array direction (displacement mode), and smaller than which particles follow the average field direction (zigzag mode) (FIG. 12). The critical size, $R_0$, may be determined by a and d, where a is the misalignment factor and d is the gap width. In the case where fields are evenly distributed in gaps, $R_0$=ad. Thus, a particle's hydrodynamic radius (size) determines which transport mode it follows. Also note that the above theory can be easily generalized for other fields, such as electrophoretic fields or pressure driven fluid flows by considering ion flows instead of fluid flows.

Figure 13:
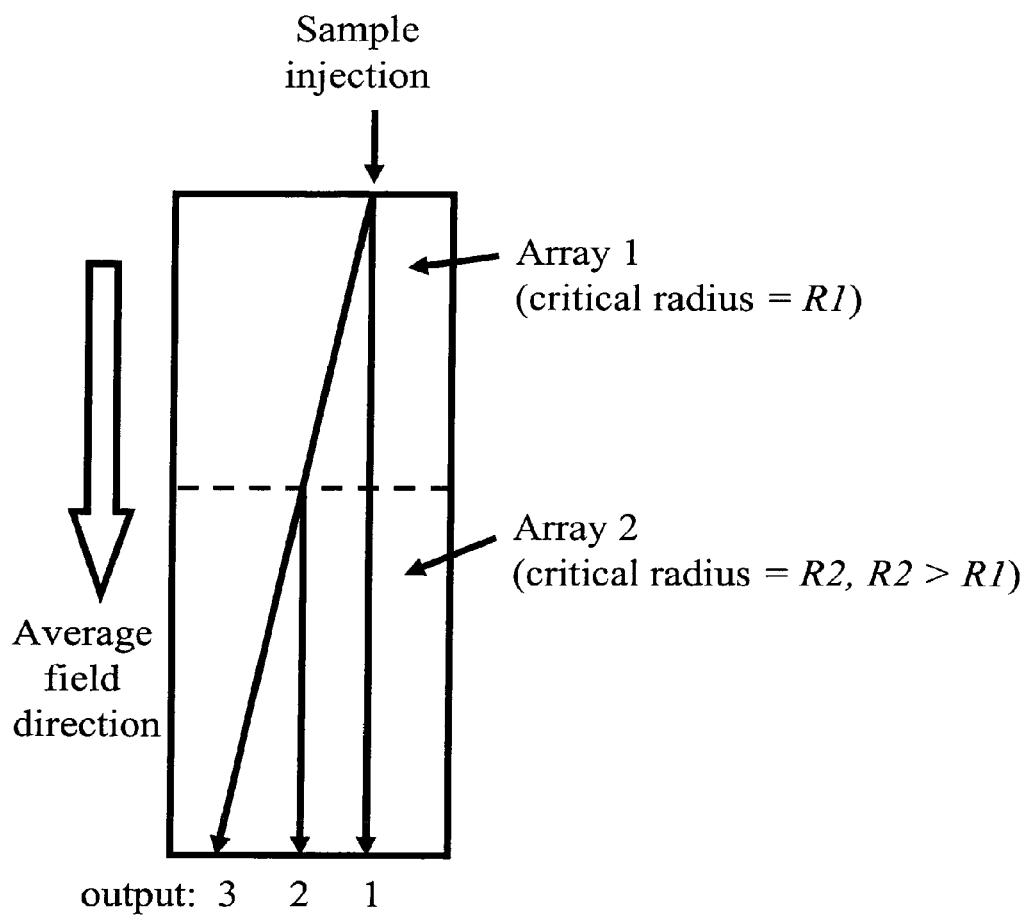
FIG. 13 shows a schematic diagram of two arrays of different critical sizes in series. Particles at output 1 are smaller than $R_1$, the critical size of the first array in the series, those at output 2 between size $R_1$ and $R_2$, and the ones at output 3 are larger than $R_2$, the critical size of the second array.

In one embodiment of the invention, the device may be employed as a filter. The term "filter" as used herein refers to a device which removes particles in certain size ranges from a fluid. The sharp transition of migration angle with respect to size is ideal for filters (FIG. 12). The micro/nano-structures of the arrays are preferably made by micro/nano-fabrication techniques. FIG. 13 shows the schematic diagram of a filter of the invention, wherein injected particles are separated into three groups of different sizes. In principle, one array can set up one critical radius (size) for particle separation, and separate a mixture of particles into two groups of particles, in one of which particles are larger than the critical size, and in the other of which particles are smaller. Two arrays of different critical sizes put together in series can separate a mixture of particles into three size ranges, large, medium, and small (FIG. 13). The sample of particles of different sizes is injected in the first array, which has a smaller critical size ($R_1$) than the second ($R_2$). While the large and medium-sized particles move in the displacement mode in the first array, the small ones move in the zigzag mode and are separated out. As particles move into the second array, the medium-sized particles switch to the zigzag mode and are separated out from the large ones. One can collect molecules of different sizes at the output of the second array, which may serve as a molecular filter and a sample preparation tool. Further, the size range of particles going to output 2, determined by $R_1$ and $R_2$, can be very narrow. For example, the device can be designed to single out only one size of DNA restriction fragments from tens or hundreds of other sizes of fragments. This device could replace the conventional techniques of gel electrophoresis and gel cutting.

Figure 14:
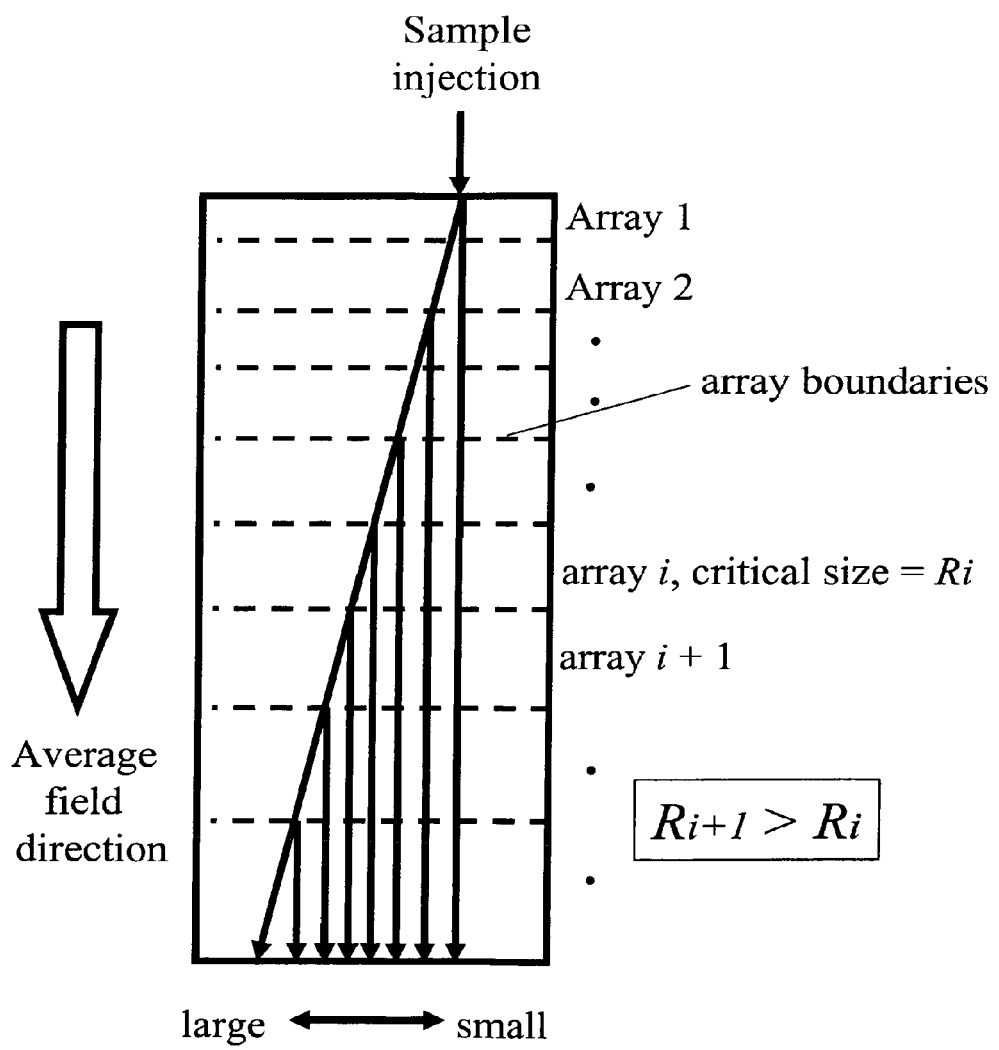
FIG. 14 shows a schematic diagram of multiple arrays in series, wherein each array has a different critical size. The dotted horizontal line represents the division between subsequent arrays and each subsequent array in the series has an increasing critical size. A continuous distribution of molecular sizes can thus be fractionated and analyzed with one device.

In another embodiment of the invention, the device of the invention may fractionate molecules according to size. High selectivity can be achieved at the sharp transition region (FIG. 12), using a single array of fixed critical radius (size). Alternatively, separation of particles in a broad size-range may require lower selectivity, which could be achieved using many arrays in series, each of which has a different critical size (FIG. 14). FIG. 14 shows a schematic diagram of multiple arrays in series, wherein each array has a different critical size. The dotted horizontal line represents the division between subsequent arrays and each subsequent array in the series has an increasing critical size. A continuous distribution of molecular sizes can thus be fractionated and analyzed with one device. In fact, smooth migration-angle-to-particle-size characteristics, including linear and exponential relationships, can be designed using many arrays in series, each having a different critical size. The critical size of an array may be adjusted by changing the gap width d, by shifting obstacles, or both.

Figure 30:
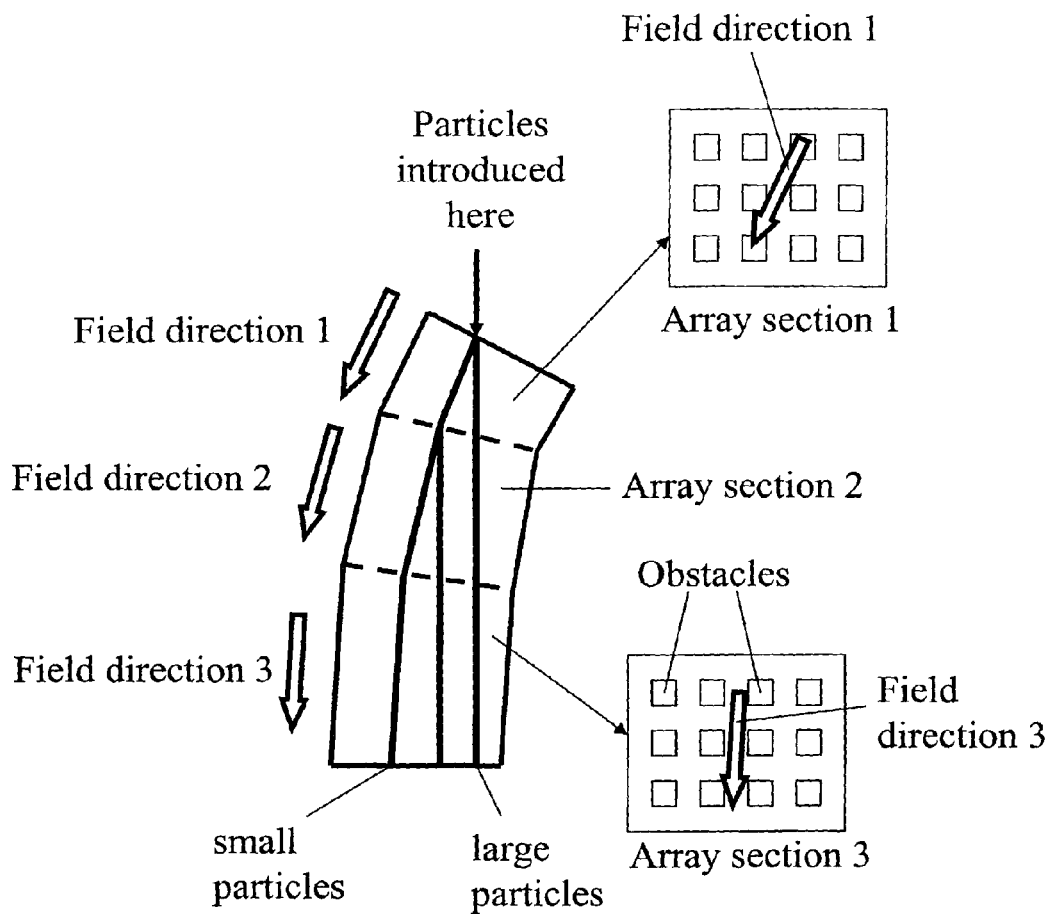
FIG. 30 shows a schematic diagram of a device having an ordered array of obstacles and employing a non-uniform field, wherein the direction of the field changes across the array.

In one embodiment of the invention, the device may comprise an ordered array of obstacles and may employ a non-uniform field, wherein the direction of the field changes across the array (FIG. 30). In one embodiment, the changing field directions may be created by a curved microfluidic channel. Since the critical size of the array depends on the field direction, the non-uniform field creates sections of array of different critical sizes. This may be desired for fractionation of particles in a broad size range. In the particular embodiment shown in FIG. 30, the field direction is large at the first array section and then reduced at the following array sections, creating a large critical size in the first section and smaller critical sizes at the following sections.

Figure 31:
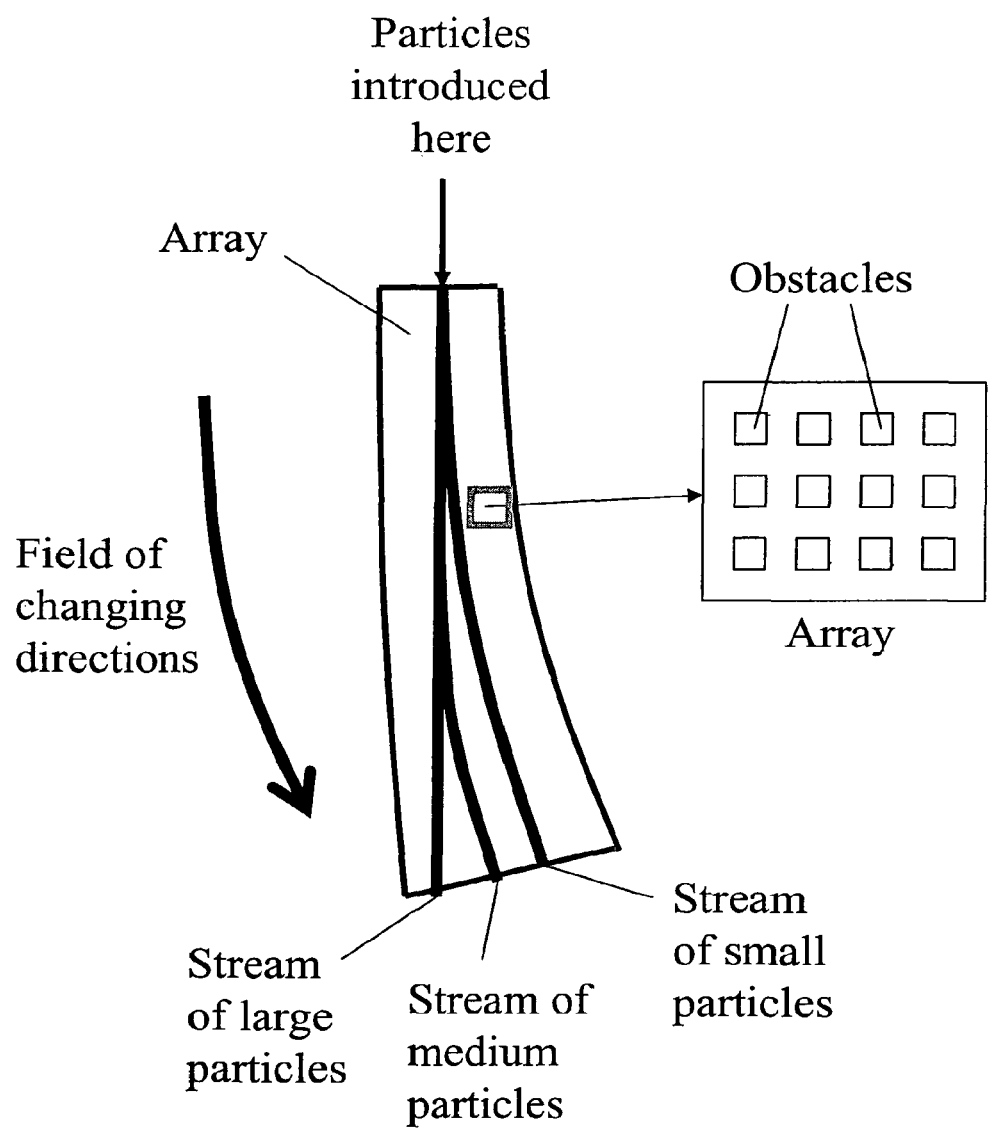
FIG. 31 shows a schematic diagram of a device having an ordered array of obstacles in a curved microfluidic channel. The curved channel may result in a field that is non-uniform.

In another embodiment of the invention, the device comprises an ordered square array of obstacles in a curved microfluidic channel (FIG. 31). The curved channel may result in a field that is non-uniform. The change in the field direction across the array creates a gradient of critical size in the array, because the critical size may depend on the field direction. Further, the field strength, another parameter that can be tuned, may be adjusted by changing the width of the microfluidic channel. This device may have better separation range and resolution than an array of one fixed critical size. A continuous gradient of critical size across the array can also be created by changing gap widths.

Figure 15:
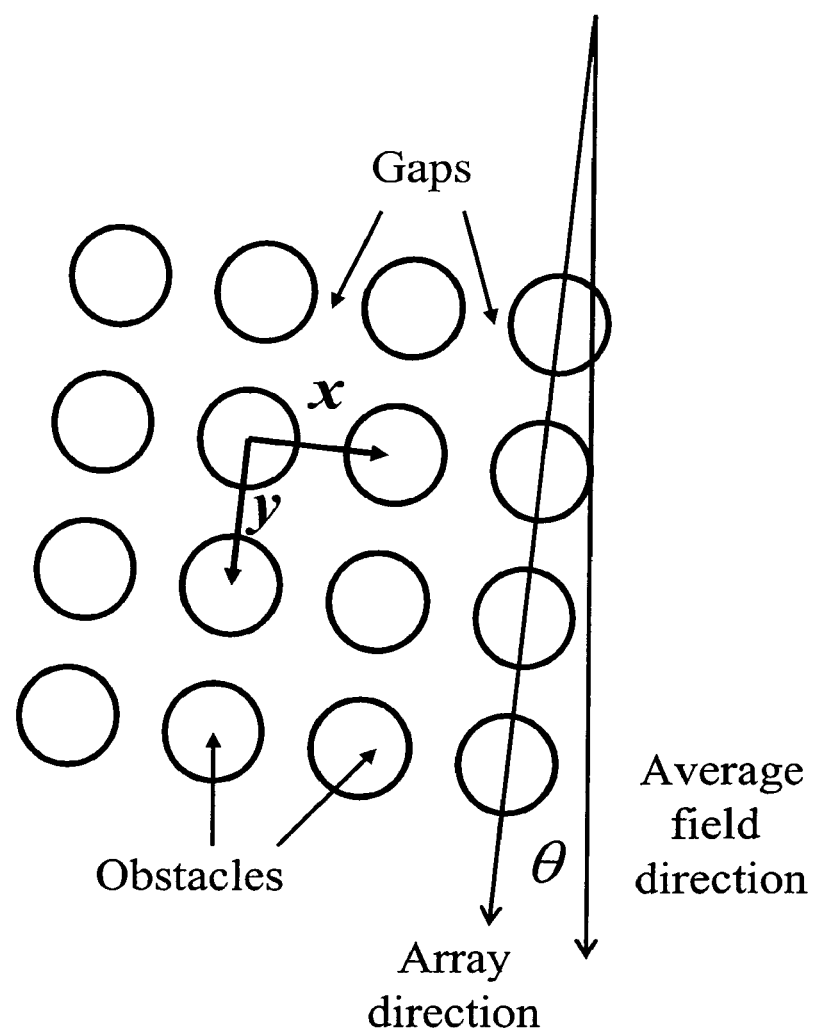
FIG. 15 shows a schematic top view of an embodiment of the invention, using a square array of circular obstacles to form the network of gaps, tilted at a small angle θ with respect to the field. The square array is spanned by primitive vectors x and y, which are perpendicular to each other. Bifurcation of field flux occurs because of the asymmetry of the obstacle array with respect to the field.

In one embodiment of the invention, the array comprises a square lattice of cylindrical obstacles, with the array tilted at an offset angle θ with respect to the field (FIG. 15). An offset angle θ of $\tan^{-1}$ (a) is equivalent to a misalignment factor of a in FIG. 6.

Figure 16:
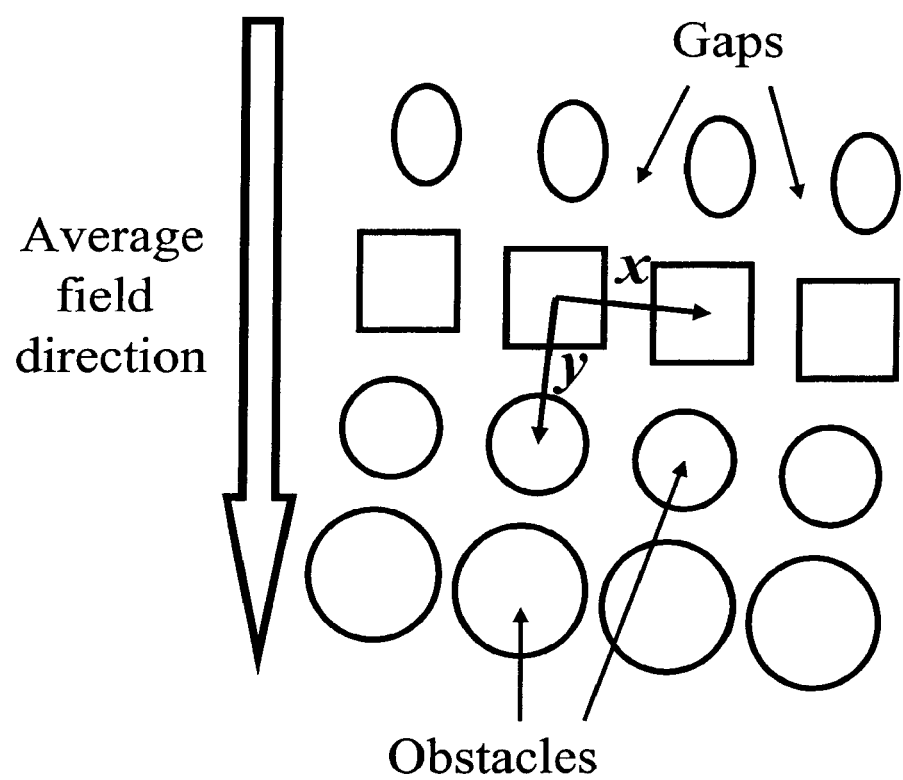
FIG. 16 shows a schematic top view of an embodiment of the invention. Each obstacle is centered at a lattice point, spanned by the primitive vectors x and y. However, the obstacles may have different shapes.

In another embodiment of the invention, the array comprising a network of gaps may be formed by a course of obstacles, which are not identical (FIG. 16). More specifically, obstacles may have different shapes or dimensions. Because the lattice on which obstacles overlay is asymmetric with respect to the field, the field flux in each gap between obstacles is divided unequally into the subsequent gaps.

Figure 17:
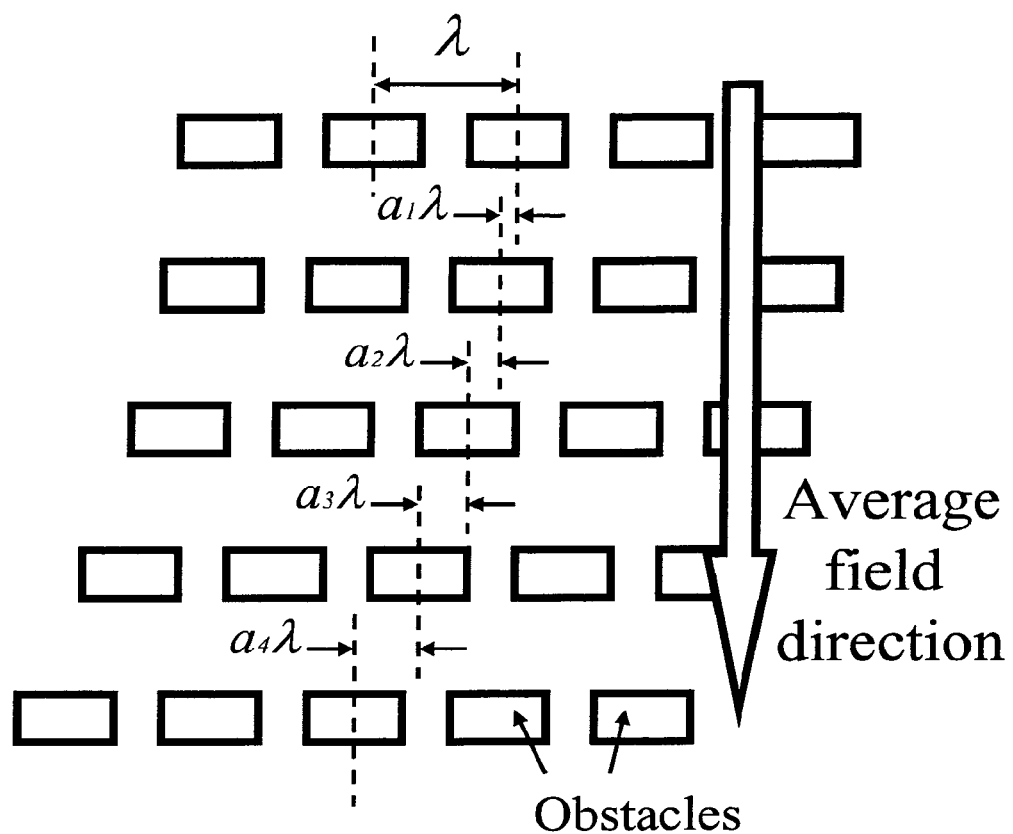
FIG. 17 shows a schematic top view of an embodiment of the invention. Every obstacle may be identical with the same horizontal period λ. However, every row of obstacles is shifted horizontally by a different amount with respect to the previous row, and the obstacle course is not a periodic lattice.

In another embodiment of the invention, the obstacle course, which forms the network of gaps, may not be a periodic lattice. For example, FIG. 17 shows a schematic top view of an embodiment of the invention in which each obstacle may be identical and have the same horizontal period λ. However, every row of obstacles is shifted horizontally by a different amount with respect to the previous row, and the obstacle course is not a Bravais lattice [N. W. Ashcroft and N. D. Mermin, Solid State Physics (Saunders College Publishing, 1976)]. Nonetheless, field flux in the array undergoes cascades of bifurcations because the obstacle course is asymmetric with respect to the average field direction. Because the critical size is dependent on the asymmetry of the field flux division, which originated from the asymmetry of the array with respect to the field, this embodiment may be useful for separating particles in a broad range.

Figure 18:
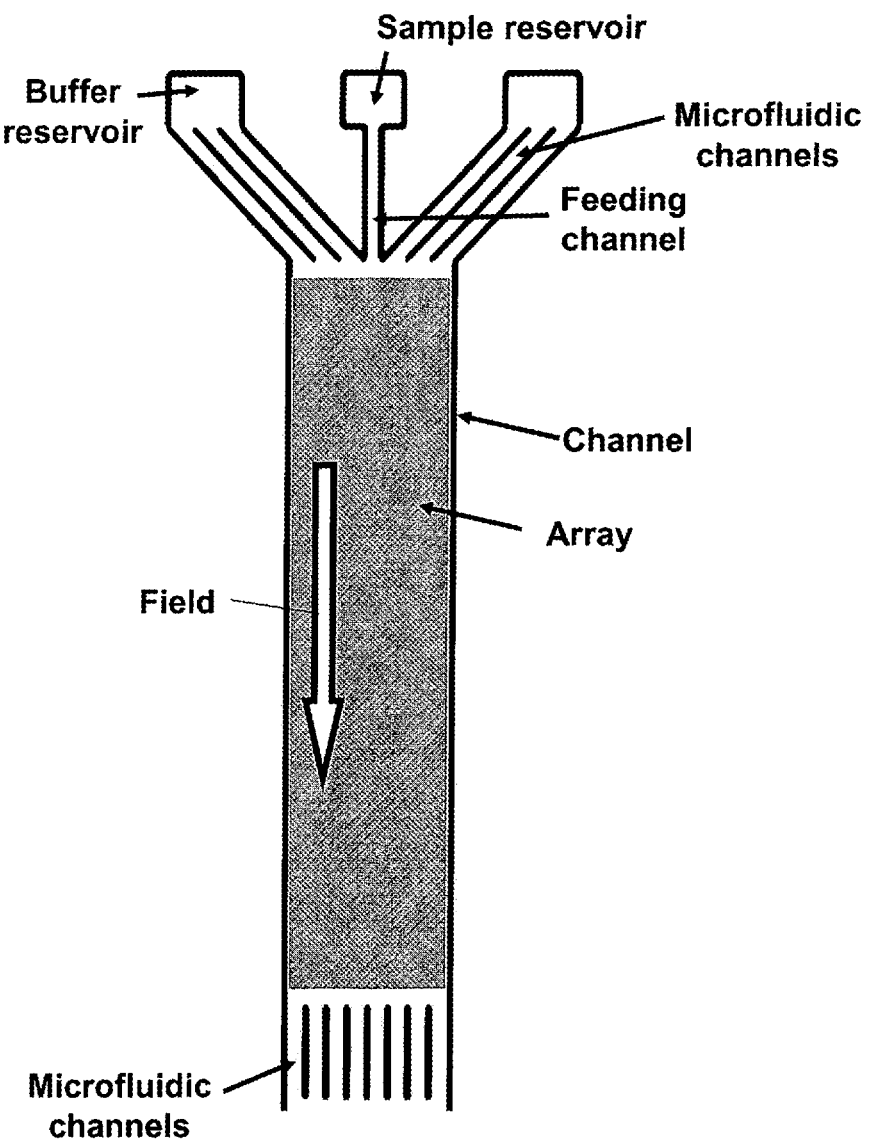
FIG. 18 shows a schematic diagram of a microfluidic device for continuous-flow separation, with sample loading structures.

In another embodiment of the invention, particles are loaded into the array using many microfluidic channels at the top of the array (FIG. 18). The many channels generate a field pattern that is generally uniform across the array. Particles are injected from one or more channels connected to one or more reservoirs containing the particles, which are to be carried across the array by the field.

In another embodiment of the invention, particles are unloaded from the array, for example via microfluidic channels at the end of the array (FIG. 18). The particles can then be routed to the next component of the microfluidic chip for further use.

Figure 27:
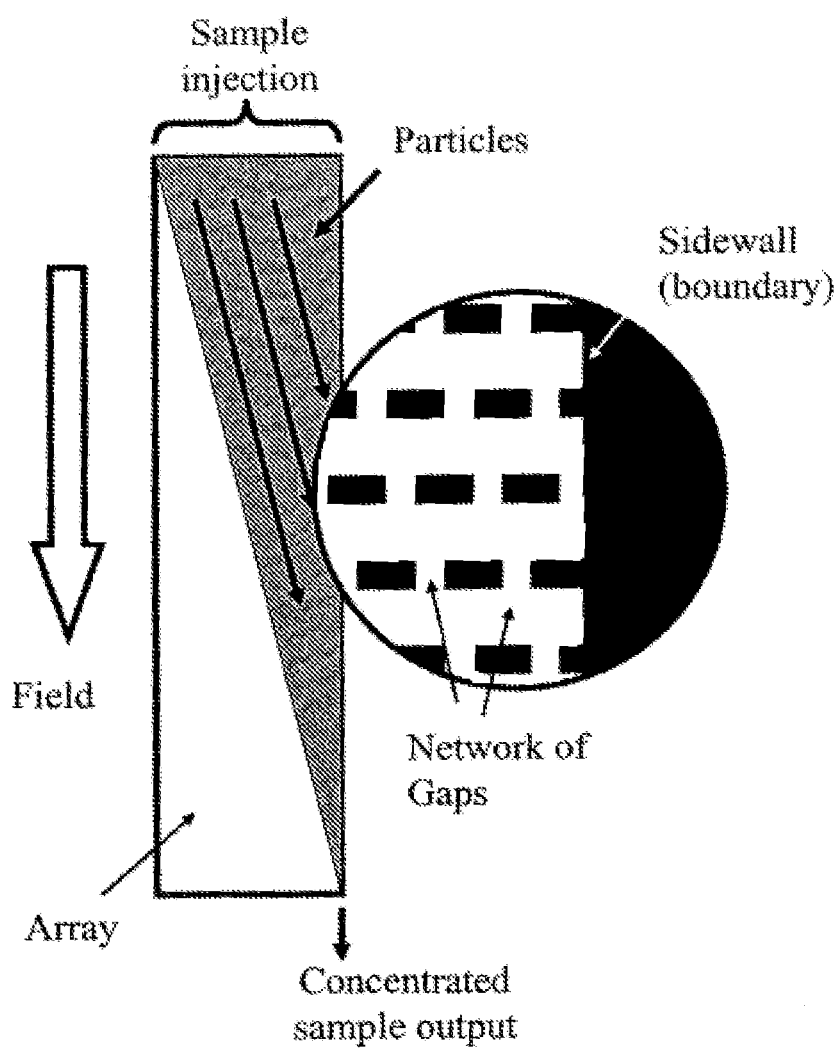
FIG. 27 shows a schematic diagram of a device used to concentrate sample. The field direction can be defined by the sidewalls of the array. The shaded area shows the trajectories of particles larger than the critical size, injected from the top. Particles move against the sidewall and are concentrated.

In another embodiment, the device of the invention can concentrate particles larger than a critical size (FIG. 27). This embodiment may exploit the array's ability to move particles off the applied field direction in displacement mode. Particles are introduced on one side of the array. Particles larger than the critical size of the array (moving in displacement mode) get piled against another boundary of the array. The device of the invention in this case acts as a concentrator. The concentrated sample can then be routed to the next component of the microfluidic chip for further use, such as creating a sample zone for fractionation. The concentrated sample can also be taken off the chip for further applications.

In a preferred embodiment of the invention, the device is micro/nano-fabricated. Microfabrication techniques may be selected from those known in the art, for example, techniques conventionally used for silicon-based integrated circuit fabrication, embossing, casting, injection molding, and so on [E. W. Becker et. al., Microelectronic Engineering 4 (1986), pages 35 to 56]. Examples of suitable fabrication techniques include photolithography, electron beam lithography, imprint lithography, reactive ion etching, wet etch, laser ablation, embossing, casting, injection molding, and other techniques [H. Becker et. al., J. Micromech. Microeng. 8 (1998), pages 24 to 28]. The microfluidic device may be fabricated from materials that are compatible with the conditions present in the particular application of interest. Such conditions include, but are not limited to, pH, temperature, application of organic solvents, ionic strength, pressure, application of electric fields, surface charge, sticking properties, surface treatment, surface functionalization, and bio-compatibility. The materials of the device are also chosen for their optical properties, mechanical properties, and for their inertness to components of the application to be carried out in the device. Such materials include, but are not limited to, glass, fused silica, silicone rubber, silicon, ceramics, and polymeric substrates, e.g., plastics, depending on the intended application.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting.

EXAMPLES

Specific representative embodiments of the invention will now be described, including how such embodiments may be made. It is understood that the specific methods, materials, conditions, process parameters, apparatus, and the like do not necessarily limit the scope of the invention.

Example 1

Figure 19:
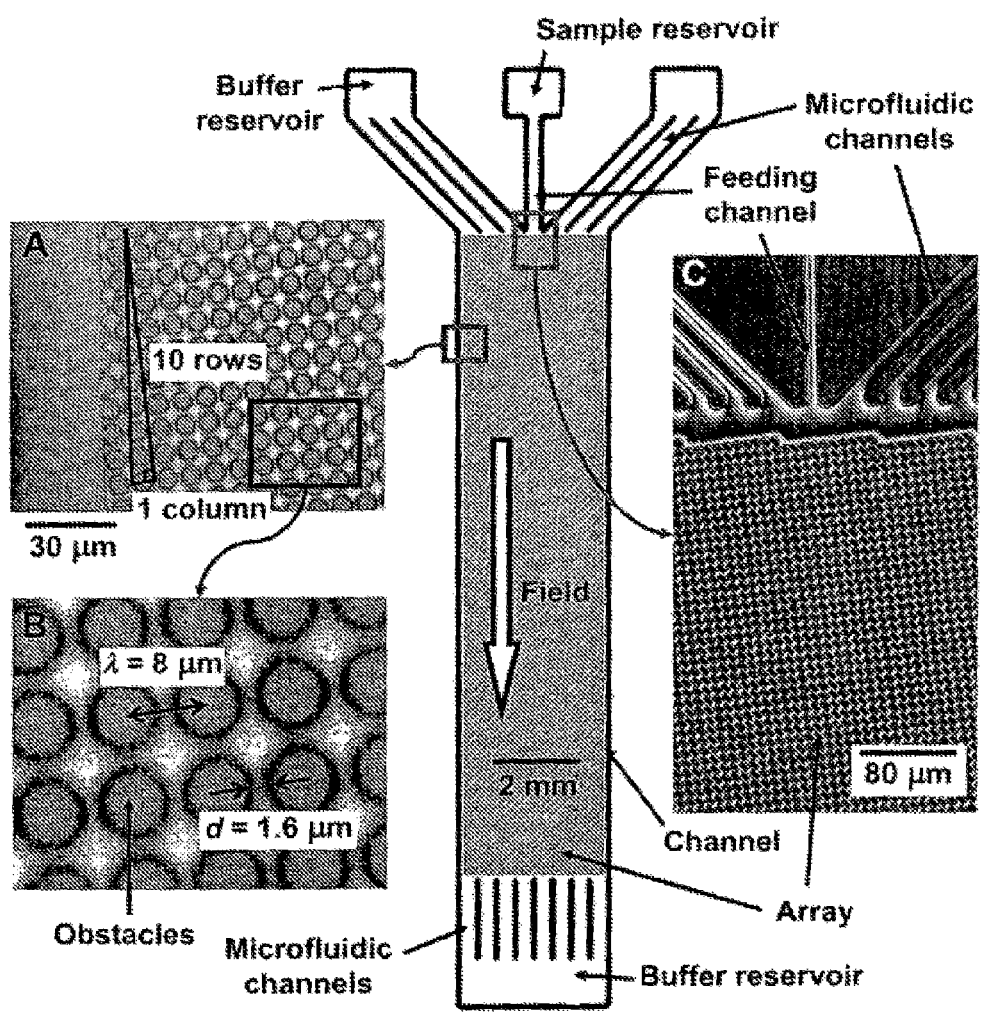
FIG. 19 shows a diagram of a microfluidic device for continuous-flow separation as constructed in Example 1.

A microfluidic device was constructed (FIG. 19). The microfluidic channel is 16 mm long, 3.2 mm wide, and 10 μm deep. The array filling the channel consists of a square lattice of cylindrical obstacles (FIG. 19, sub-view A), where the center-to-center distance, λ is 8 μm, and the spacing d between the obstacles 1.6 μm (FIG. 19, sub-view B). The field employed here is a pressure driven field flow. The lattice is rotated by 5.7° ($\tan^{-1}$ 0.1) with respect to the channel (FIG. 19, sub-view A), which defines the flow direction. The rotation of $\tan^{-1}$ 0.1 corresponds to a=0.1 thus a complete pitch λ is shifted every 10 rows (FIG. 19, sub-view A). In principle, this configuration provides 10 slots, rather than the 3 discussed above. Particles are injected from a 10 μm-wide channel and carried across the array by a pressure-driven flow, which is made uniform by the many channels on the top and bottom of the array (FIG. 19, sub-view C). The microfluidic channels and the array were fabricated on a silicon wafer using photolithography and deep reactive ion etching, techniques conventionally used for silicon-based integrated circuit fabrication. Holes through wafers for fluid access were drilled before sealing with a glass coverslip coated with silicone rubber (RTV-615 from General Electric) to sandwich the array.

The two transport modes were experimentally observed using fluorescent polystyrene microspheres of 0.40 μm and 1.03 μm in aqueous buffer (FIG. 20, sub-view A) (0.1.times.ris-Borate-EDTA buffer containing 0.02% POP-6, a performance-optimized linear polyacrylamide (Perkin-Elmer Biosystems), was used in the experiments). The image was taken by fluorescent microscopy with a long exposure time to show trajectories of individual particles. The varying brightness along the trajectory reflects the different flow speeds of a microsphere in the array, dimmer in the narrow gaps due to higher flow speed and lower residence time. As predicted, the 0.40 μm microsphere (left) crossed a column of obstacles every 10 rows in the zigzag mode, whereas the 1.03 μm microsphere (right) was channeled along the axis of the obstacle array in the displacement mode.

Figure 20:
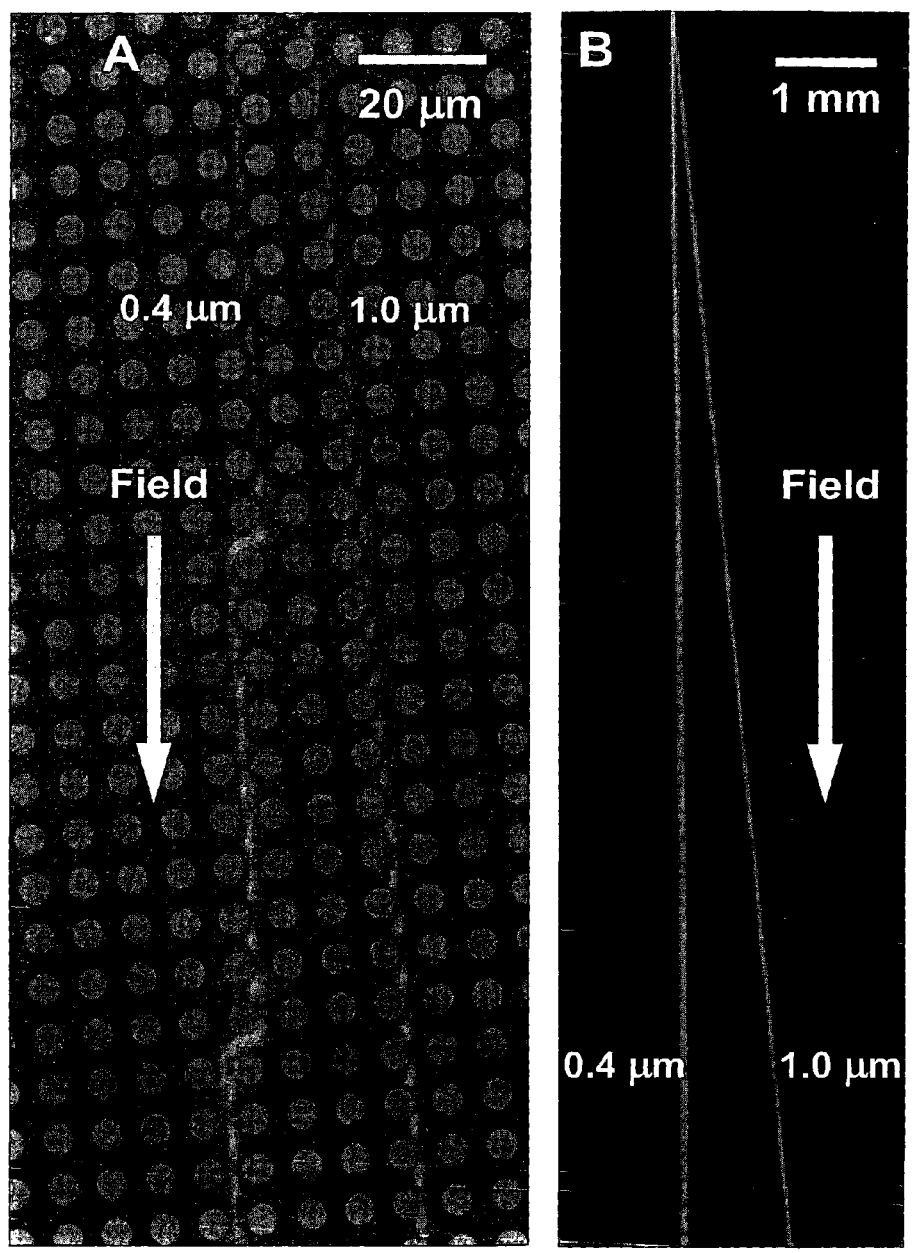
FIG. 20 shows fluorescent images of microspheres migrating in the obstacle array, showing (A) the two transport modes for (B) the separation of microspheres with no dispersion. The gray dots in (A), which represent the obstacles, have been superimposed on the fluorescent image.

FIG. 20, sub-view B shows the continuous-flow separation of 0.40 μm and 1.03 μm microspheres injected into the array from a feed channel at the top. In this image many trajectories were superimposed. The 0.40 μm and 1.03 μm spheres migrated at ~0° (flow direction) and ~5.7° (array rotation) respectively relative to the flow direction, as expected. The pressure used to drive the flow was 30 kPa, which created an average flow speed of ~400 μm/s. The running time through the device was ~40 s.

Figure 21:
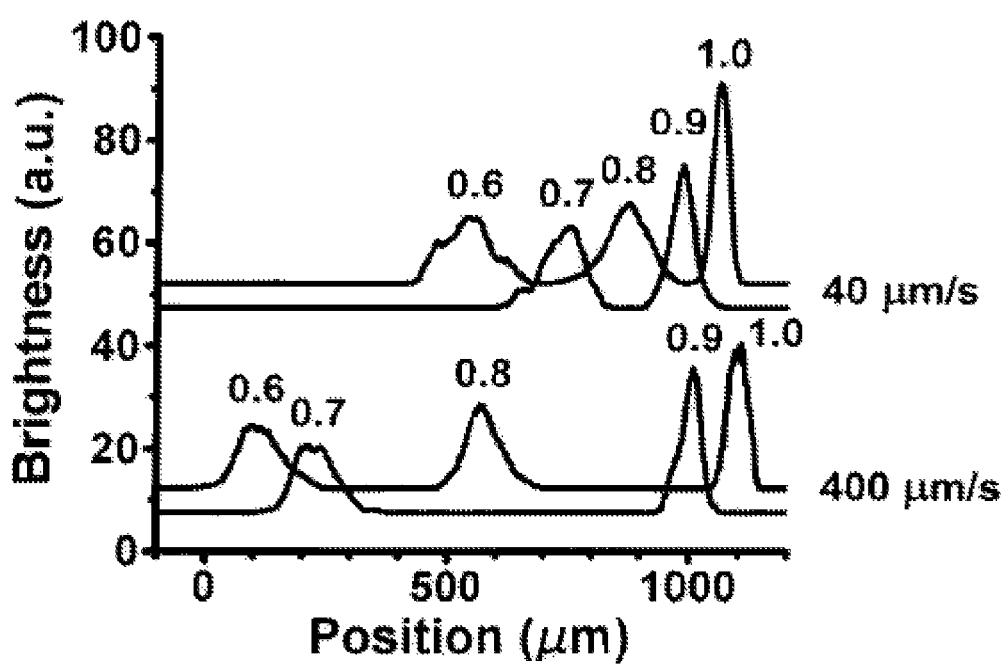
FIG. 21 shows the fluorescent profiles of microspheres separated using flow speeds of ~40 μm/s (upper curves) and ~400 μm/s (lower curves) scanned at ~11 mm from the injection point. The 0.60 μm, 0.80 μm, and 1.03 μm diameter beads are green-fluorescent, while 0.70 μm and 0.90 μm are red, and thus each scan is shown as two curves representing the two colors.

To probe the resolution of the device, fluorescent microspheres of 0.60 μm, 0.70 μm, 0.80 μm, 0.90 μm and 1.03 μm diameter were mixed and injected into the array (The concentrations of the microspheres of 0.60 μm, 0.70 μm, 0.80 μm, 0.90 μm and 1.03 μm were 0.015%, 0.010%, 0.010%, 0.005%, and 0.005% solid, respectively). The beads were separated into different streams using a flow speed of ~40 μm/s, created by a driving pressure of 3 kPa. The fluorescence profile scanned 11 mm from the injection point is shown in FIG. 21. The measured migration directions with respect to the flow (field), defined as the migration angles, are plotted as a function of the microsphere size in FIG. 22, which shows that under this flow speed (~40 μm/s), the transition from the zigzag to the displacement mode is gradual. The smooth transition is probably due to Brownian motion of the particles between streamlines. At a flow speed of 40 μm/s, a 0.6 μm particle—diffusion coefficient in water of 0.73 μm$^2$ is (H. C. Berg, Random Walks in Biology, Princeton University Press, New Jersey, 1993, p. 56)—has a diffusion length of ~0.54 μm over the 0.2 s it takes to move the 8 μm from one row of obstacles to the next. This is a factor of 3 larger than the average slot width of ~0.16 μm.

Figure 22:
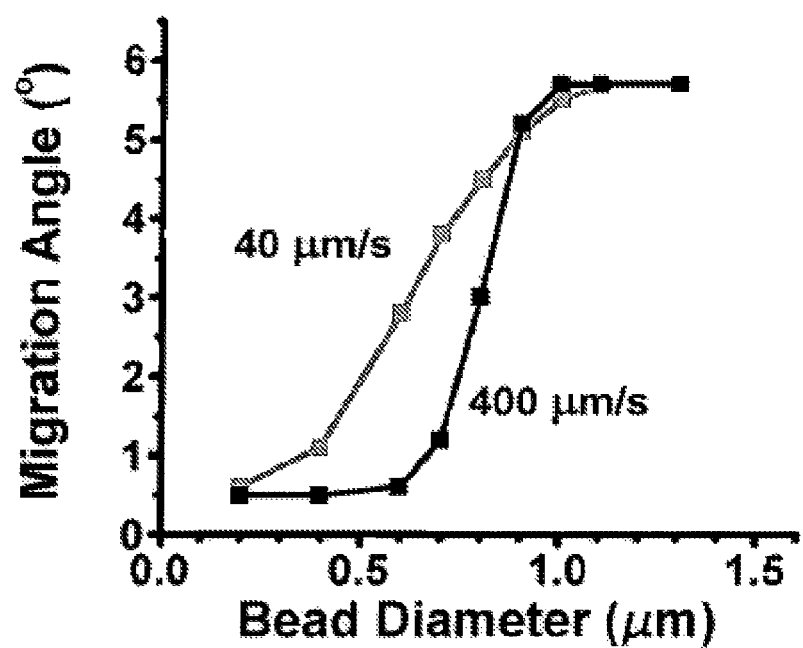
FIG. 22 shows the measured migration angles as a function of microsphere diameter at two different flow speeds.

To minimize the effects of Brownian motion, the Peclet number was increased by increasing the flow speed. Peclet number (Pe) is defined as Pe=vd/D, where v is the flow speed, d is the characteristic dimension of the array, and D the diffusion coefficient of the particle being separated. FIG. 22 shows a sharper transition when the flow speed is increased by a factor of 10 (~400 μm/s), created by a driving pressure of 30 kPa. The high flow speed not only increases the selectivity so that the device becomes more sensitive to size changes, but also shortens the running time to ~40 s. The transition occurs approximately at 0.8 μm (FIG. 22). The size coefficients of variation (CV) of the best monodispersed microspheres commercially available are 1.3%, 1.0% and 1.0% for 0.70 μm, 0.80 μm and 0.90 μm, respectively, as measured by the manufacturer. The coefficient of variation (CV) of particle diameter Φ is defined as CV=ΔΦ/<Φ>*100%, where ΔΦ is the standard deviation of Φ, and <Φ> the mean of Φ. The peak widths measured at 11 mm from the injection point, correspond to CV's of 2.5%, 1.2% and 0.9% for these three sizes, respectively (FIG. 21). CV's are calculated according to: CV=dΦ/dx*Δx/<Φ>*100%, where x is the lateral position of the band and Δx the measured standard deviation (half-width). Note that the measured peaks of 0.80 μm and 0.90 μm are as sharp as the size-variances of the microspheres themselves, and thus band broadening in our device is less than the known variance in particle size.

Example 2

Figure 23:
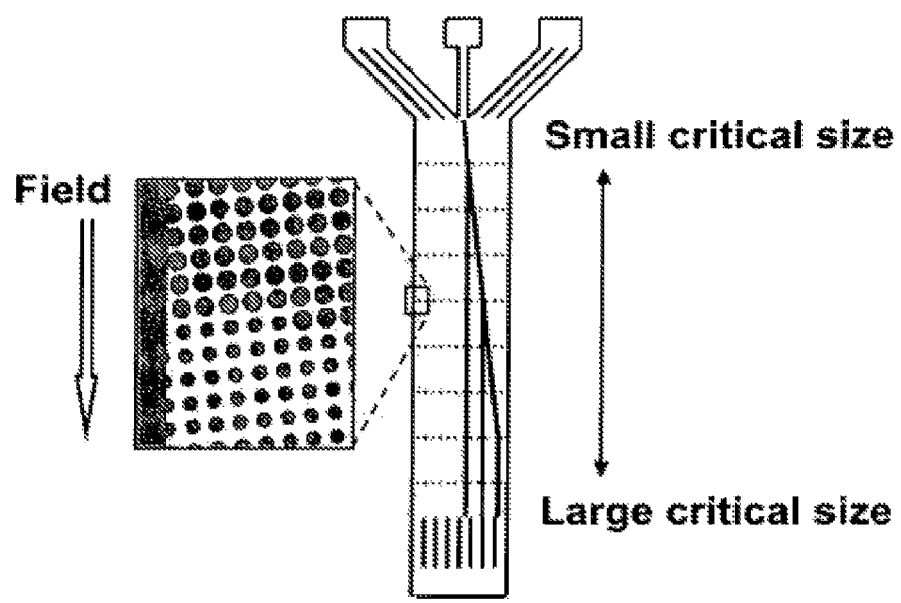
FIG. 23 shows a schematic diagram of a device for particle separation comprising an array having 9 sections (divided by dotted lines) of different critical sizes, and sample loading structures. While the orientation and the lattice constants of the array are kept the same, the obstacle diameters are changed to create different-sized gaps d and critical sizes.
Figure 24:
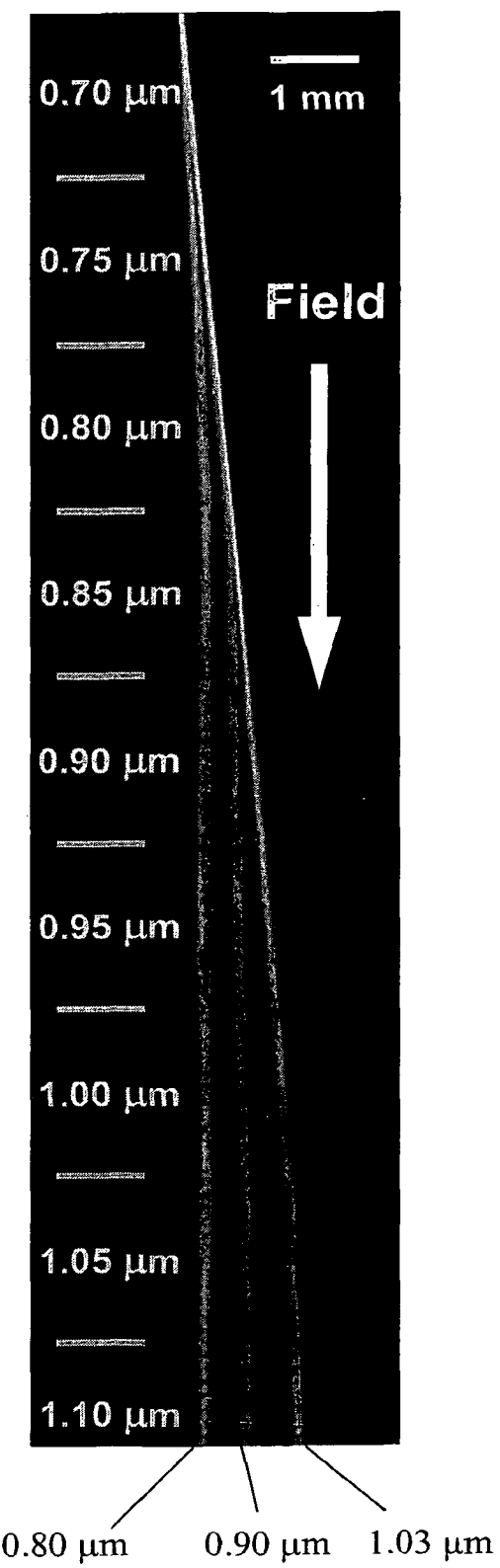
FIG. 24 shows the high-resolution separation of fluorescent microspheres of 0.80 μm (left), 0.90 μm (center) and 1.03 μm (right), using an array of varying gap size. While the orientation and the lattice constants of the array are kept the same, the obstacle diameters are changed to create different-sized gaps d, labeled on the left side of the fluorescent image. Individual 1.03 μm streamlines clearly show zigzag migration.

One advantage of the flexibility of microfabrication is that the array can be designed to have varying gap widths as a function of distance, thereby optimizing separation for complex mixtures. To demonstrate this point, a device was fabricated containing 9 sections, each of which had a different gap width, starting with 1.4 μm and ending with 2.2 μm in increments of 0.1 μm (FIG. 23 and FIG. 24). The varying gap widths were designed to tune the critical diameter in 9 stages from ~0.70 μm to ~1.10 μm, so that a given sized particle would switch from displacement mode to zigzag mode as the gap width increased.

A mixture of monodisperse (CV=1%) microspheres of 0.80 μm, 0.90 μm and 1.03 μm was injected from the small-gap side of the array (FIG. 23 and FIG. 24), and flown at ~400 μm/s using a driving pressure of 30 kPa. Initially, all microspheres were larger than the critical size, and migrated at the same angle with respect to the vertical flow (displacement mode). Soon, however, the 0.80 μm microspheres (left) switched to the flow direction (vertical), presumably in zig-zag mode. 0.90 μm microspheres switched to vertical at the fourth section, and the 1.03 μm microspheres made the transition around the eighth section. The fluorescent intensity profile was scanned at ~14 mm from the injection point (FIG. 25), and showed that the 0.80 μm, 0.90 μm and 1.03 μm peaks had CV's of 1.1%, 1.2% and 1.9%, respectively (see the scale bars, centered at the means of the peaks). By comparison, the 1% CV attributable to nonuniformity in the microsphere population is shown as the black scale bars underneath the peaks. Note that a fraction of the 1.03 μm microspheres were separated out from the main peak and formed a sub-band, most likely because of the non-homogeneity in the microsphere population. Again, the peaks are virtually resolved to the mono-dispersity of the most uniform microspheres commercially available. The running time was ~40 s.

Figure 25:
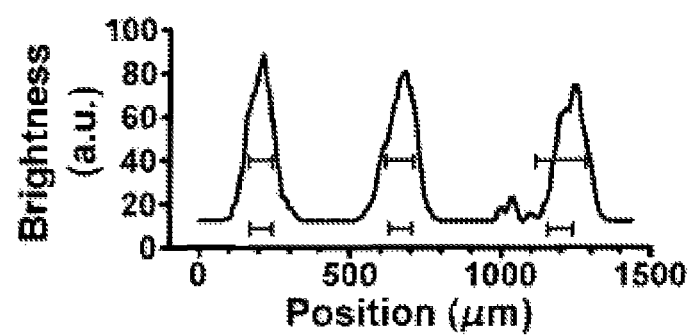
FIG. 25 shows the fluorescent profile of the separated particles scanned at 14 mm from the injection point.

The results of FIG. 21 and FIG. 25 suggest that the resolution of the device may exceed our ability to measure it. One could in principle discover the limits of resolution for the approach by exploring the resolving power of the current array with a series of size classes varying in approximately 0.01 μm intervals around ~1 μm, each class with a CV of ~0.1%.

Example 3

A device having identical array dimensions and loading structures as in Example 1 was constructed for separation of nucleic acids according to molecular weight. The device was made of fused silica instead of silicon using the same techniques as described in Example 1. Electric fields, instead of pressure-driven fluid flow, were used as the field. A mixture of coliphage λ and T2 dsDNA (48.5 kb and 164 kb respectively) at ~2 μg/ml and ~1 μg/ml was used as a test sample, and visualized by fluorescent microscopy. DNA was stained with TOTO-1 (Molecular Probes) at a ratio of 1 dye molecule per 10 base pairs. 0.1% POP-6, a performance-optimized linear polyacrylamide (Perkin-Elmer Biosystems), and 10 mM dithiothreitol (DTT) were added to the ½.times. Tris-Borate-EDTA buffer to suppress electro-osmotic flow and photo-bleaching, respectively. The electric fields were applied using electrodes immersed in buffer reservoirs. The migration speeds of the molecules were controlled by the voltage applied to the reservoirs, and measured by observing the velocity of individual molecules.

Figure 26:
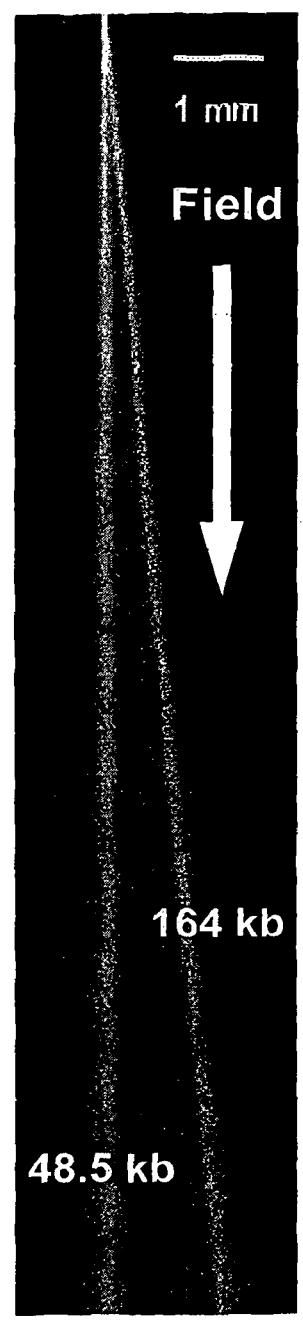
FIG. 26 shows of fluorescent image of DNA molecules separated according to size using a device of the present invention. Molecules are introduced at the top of the figure.

The two species were separated with good resolution using an electric field of ~5 V/cm (FIG. 26).

Example 4

Figure 28:
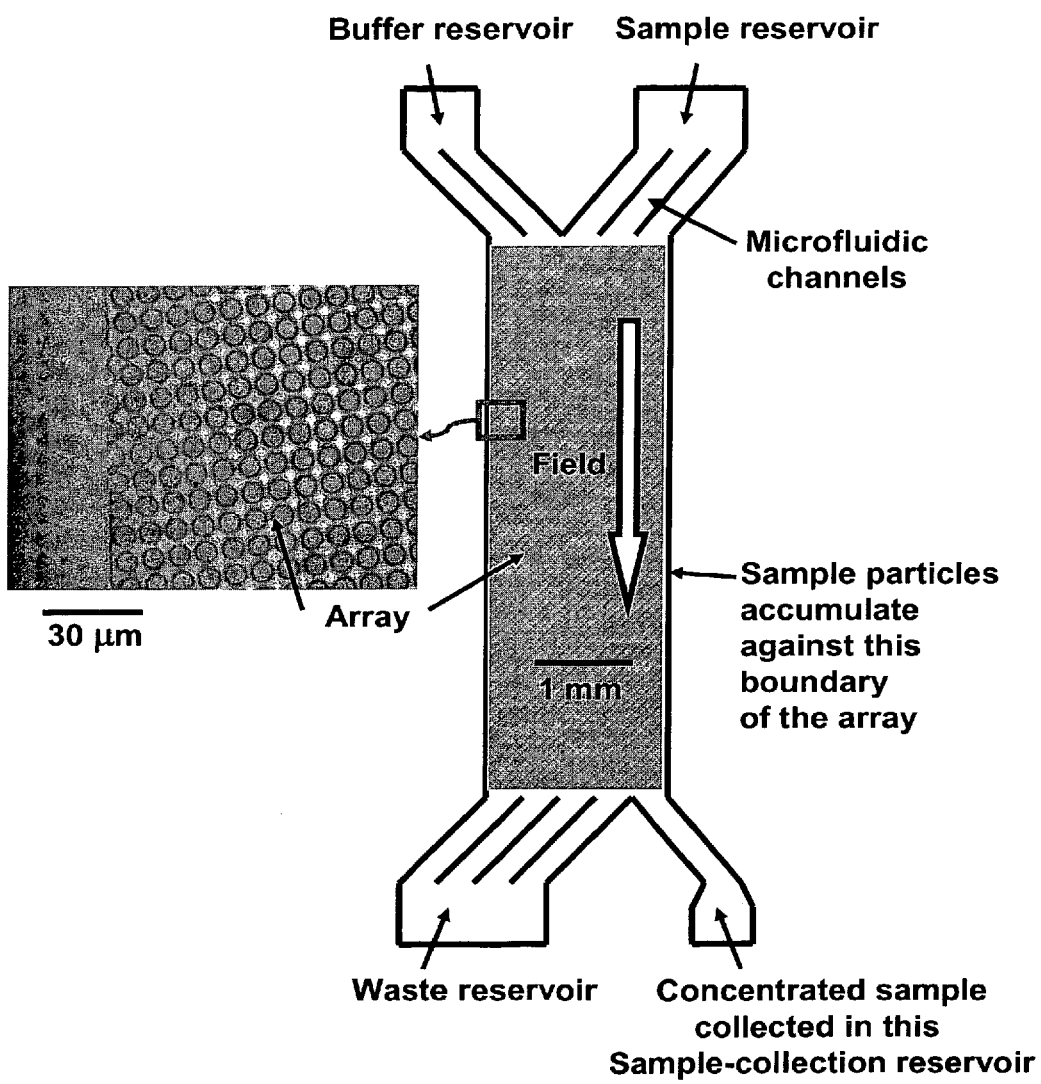
FIG. 28 shows a schematic diagram of a device for concentrating particles. The device comprises an array, which moves particles against a boundary of the array, and microfluidic channels and reservoirs for sample loading and collection.
Figure 29:
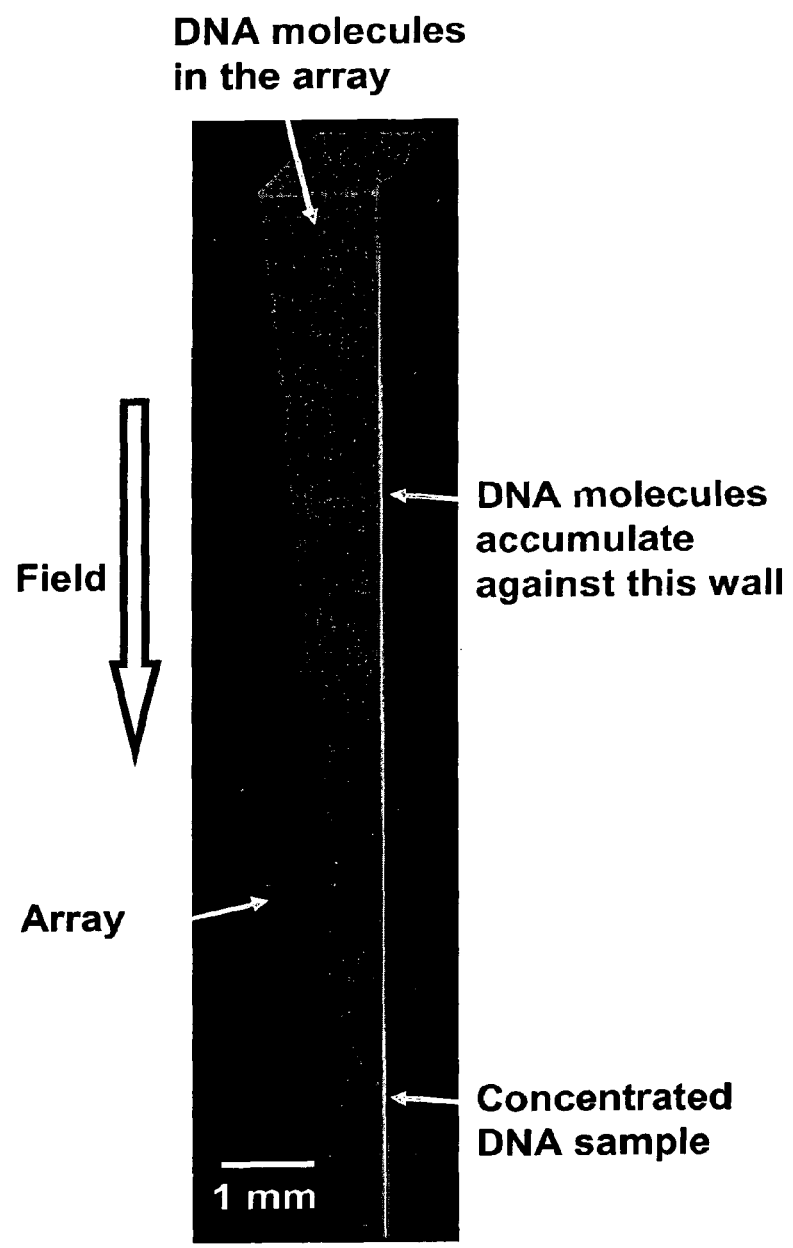
FIG. 29 shows of fluorescent image of DNA molecules getting concentrated against a boundary of the array. DNA samples were introduced from the top of the picture.

A device of the present intervention for concentrating DNA molecules is made and schematically shown in FIG. 28. The device comprises an array and microfluidic channels for sample injection and extraction, which are identical in dimensions with Example 1. The field used herein is an electric field, applied using electrodes immersed in the buffer fluid reservoirs. The device is made of fused silica using techniques described in Example 1. Coliphage T2 DNA at ~1 μg/ml in ½x. Tris-Borate-EDTA buffer containing 0.1% POP-6, a performance-optimized linear polyacrylamide (Perkin-Elmer Biosystems) and 10 mM dithiothreitol (DTT), was used as a test sample. The DNA was loaded onto the device at the sample reservoir, and concentrated against a boundary of the array to ~120 μg/ml (FIG. 29). The electric field strength was ~5 V/cm. The concentrated sample is removed from the array and collected in the sample-collection reservoir (FIG. 28).

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. A device comprising:
an array of obstacles within a microfluidic channel, wherein said array of obstacles comprises obstacles arranged in rows and columns, and the device employs a field that propels particles through the microfluidic channel and said rows and columns are asymmetrically tilted with respect to the average direction of the field, such that, when particles are introduced into the array, particles having a size less than a predetermined critical size are transported in a first direction, and particles having a size at least that of the critical size are transported in a second direction, and wherein the first and second directions are different.

2. The device of claim 1, the device further comprising a buffer source at a beginning of said microfluidic channel.

3. The device of claim 1, the device further comprising a sample source at a beginning of said microfluidic channel.

4. The device of claim 1, the device further comprising an unloading channel at an end of said microfluidic channel.

5. The device of claim 1, the device further comprising a concentrated sample reservoir at an end of said microfluidic channel.

6. The device of claim 1, the device further comprising a plurality of concentrated sample reservoirs at an end of said microfluidic channel, wherein each sample reservoir receives a different size range of particles.

7. The device of claim 1, wherein at two adjacent obstacles in at least one row are separated by 8 μm center-to-center.

8. The device of claim 1, wherein said asymmetric tilt is at an offset angle of 5.7° with respect to the direction of the field.

9. The device of claim 1, wherein each subsequent row of obstacles is shifted laterally with respect to the previous row by between 0.0 to 0.5 times the distance, center-to-center, of adjacent obstacles in a row.

10. The device of claim 1, wherein each subsequent row of obstacles is shifted laterally with respect to the previous row by one-third the distance, center-to-center, of adjacent obstacles in a row.

11. The device of claim 1, wherein at least one row of obstacles comprises differently shaped obstacles than at least one other row of obstacles.

12. The device of claim 1, wherein said array of obstacles comprises a plurality of sub-arrays of obstacles, and wherein at least one sub-array of obstacles is different than at least one other sub-array of obstacles.

13. The device of claim 1, wherein said microfluidic channel is curved.

14. The device of claim 1, wherein the field comprises a plurality of sub-fields, and wherein at least one sub-field has a different average direction of at least one other sub-field.

15. A method comprising:
introducing particles into an array of obstacles within a microfluidic channel, wherein said array of obstacles comprises obstacles arranged in rows and columns, and the device employs a field that propels particles through the microfluidic channel said rows and columns are asymmetrically tilted with respect to the average direction of the field, such that, when particles are introduced into the array, particles having a size less than a predetermined critical size are transported in a first direction, and particles having a size at least that of the critical size are transported in a second direction, and wherein the first and second directions are different.

16. The method of claim 15, wherein the method further comprises introducing a buffer into the microfluidic channel.

17. The method of claim 15, wherein the method further comprises retrieving the particles having a size at least that of the critical size.

18. The method of claim 15, wherein the method further comprises retrieving the particles having a size less than the critical size.

19. The method of claim 15, wherein the method further comprises retrieving particles from a plurality of concentrated sample reservoirs at an end of said microfluidic channel, wherein each sample reservoir receives a different size range of particles.

20. The method of claim 15, wherein the method further comprises providing the field such that the field comprises a plurality of sub-fields, and wherein at least one sub-field has a different average direction of at least one other sub-field.

* * * * *